(12) United States Patent
Truitt et al.

(10) Patent No.: US 7,771,383 B2
(45) Date of Patent: Aug. 10, 2010

(54) FLUID CONTROL DEVICE WITH VALVE AND METHODS OF USE

(75) Inventors: Tim L. Truitt, Orange, CA (US); Alex Truman Mazza, Grand Terrace, CA (US)

(73) Assignee: Medegen, Inc., Scottsdale, AZ (US)

(*) Notice: Subject to any disclaimer, the term of this patent is extended or adjusted under 35 U.S.C. 154(b) by 1300 days.

(21) Appl. No.: 10/972,312

(22) Filed: Oct. 22, 2004

(65) Prior Publication Data
US 2006/0089603 A1   Apr. 27, 2006

(51) Int. Cl.
A61M 1/00   (2006.01)
A61M 5/00   (2006.01)

(52) U.S. Cl. .......................................... 604/32; 604/246

(58) Field of Classification Search ................ 604/32
See application file for complete search history.

(56) References Cited

U.S. PATENT DOCUMENTS

| | | | | |
|---|---|---|---|---|
| 3,610,228 | A | | 10/1971 | Temkin ...................... 600/561 |
| 3,774,604 | A | | 11/1973 | Danielsson ............. 604/167.05 |
| 3,780,736 | A | * | 12/1973 | Chen ........................... 604/32 |
| 3,934,576 | A | | 1/1976 | Danielsson ................. 600/487 |
| 3,952,729 | A | * | 4/1976 | Libman et al. .............. 600/575 |
| 4,219,021 | A | * | 8/1980 | Fink .......................... 137/556.6 |
| 4,326,569 | A | | 4/1982 | Vaillancourt ................. 141/383 |
| 4,353,243 | A | * | 10/1982 | Martin ....................... 73/23.42 |
| 4,447,235 | A | | 5/1984 | Clarke ........................ 604/169 |
| 4,566,480 | A | | 1/1986 | Parham ...................... 137/271 |
| 4,763,648 | A | | 8/1988 | Wyatt ......................... 128/673 |
| 4,808,168 | A | | 2/1989 | Warring ...................... 604/158 |
| 4,865,583 | A | | 9/1989 | Tu .............................. 604/53 |
| 4,920,970 | A | | 5/1990 | Wyatt ......................... 128/673 |
| 4,950,230 | A | * | 8/1990 | Kendell ...................... 604/28 |

(Continued)

FOREIGN PATENT DOCUMENTS

EP   1234596   8/2002

(Continued)

OTHER PUBLICATIONS

Supplementary Partial European Search Report issued for European Patent Application No. 05814886.7, dated Jun. 23, 2009, 9 pages.

Primary Examiner—Nicholas D Lucchesi
Assistant Examiner—Jason Flick
(74) Attorney, Agent, or Firm—Fulbright & Jaworski L.L.P.

(57) ABSTRACT

A fluid control device for directing fluid flow comprising a needleless access device for transferring fluids and methods of directing fluid flow. The fluid control device may have a first port, a second port, a third port and a connecting portion joining the first, second and third ports. A first valve element may be positioned within the first port and a fluid director may be positioned within the connecting portion. The first valve element may move between an opening position, where fluid may flow past the first valve element, and a closed position, where fluid may be prevented from flowing past the first valve element. The fluid director may have at least one passageway for connecting at least two of the first, second and third ports such that fluid may flow therebetween. An actuation mechanism may be used to orient the fluid director and, consequently, the at least one passageway within the connecting portion.

46 Claims, 20 Drawing Sheets

U.S. PATENT DOCUMENTS

| | | | |
|---|---|---|---|
| 4,981,140 A * | 1/1991 | Wyatt | 600/486 |
| 5,002,066 A | 3/1991 | Simpson et al. | 128/760 |
| 5,002,528 A | 3/1991 | Palestrant | 604/28 |
| 5,078,688 A | 1/1992 | Lobodzinski et al. | 604/164 |
| 5,144,972 A | 9/1992 | Dryden | 137/15 |
| 5,396,899 A | 3/1995 | Strittmatter | 128/763 |
| 5,468,230 A | 11/1995 | Corn | 604/180 |
| 5,593,385 A | 1/1997 | Harrison et al. | 604/83 |
| 5,645,538 A | 7/1997 | Richmond | 604/256 |
| 5,704,914 A | 1/1998 | Stocking et al. | 604/164 |
| 5,782,816 A | 7/1998 | Werschmidt et al. | |
| 5,848,994 A | 12/1998 | Richmond | 604/248 |
| 5,865,808 A | 2/1999 | Corn | 604/174 |
| 5,897,497 A | 4/1999 | Fernandez | 600/435 |
| 6,068,617 A | 5/2000 | Richmond | 604/255 |
| 6,099,511 A | 8/2000 | Devos et al. | 604/246 |
| 6,106,502 A | 8/2000 | Richmond | 604/246 |
| 6,113,068 A | 9/2000 | Ryan | 251/149.4 |
| 6,158,467 A | 12/2000 | Loo | 137/625.47 |
| 6,287,265 B1 | 9/2001 | Gleason | 600/573 |
| 6,299,131 B1 | 10/2001 | Ryan | 251/149.4 |
| 6,364,869 B1 | 4/2002 | Bonaldo | 604/537 |
| 6,371,942 B1 | 4/2002 | Schwartz et al. | 604/246 |
| 6,418,966 B2 | 7/2002 | Loo | 137/625.47 |
| 6,457,488 B2 * | 10/2002 | Loo | 137/625.47 |
| 6,468,251 B1 | 10/2002 | Yamanaka et al. | 604/256 |
| 6,485,472 B1 | 11/2002 | Richmond | 604/246 |
| 6,635,020 B2 | 10/2003 | Tripp et al. | 600/488 |
| 6,638,258 B2 | 10/2003 | Schwartz et al. | 604/246 |
| 2001/0049508 A1 | 12/2001 | Fangrow et al. | 604/249 |
| 2003/0060779 A1 | 3/2003 | Richmond | 604/246 |
| 2003/0181850 A1 | 9/2003 | Diamond et al. | 604/246 |

FOREIGN PATENT DOCUMENTS

| | | |
|---|---|---|
| GB | 2274148 | 7/1994 |
| JP | 4354952 | 12/1992 |
| JP | 6030905 | 2/1994 |
| JP | 7100212 | 4/1995 |
| JP | 2003033441 | 2/2003 |
| WO | WO 9415664 | 7/1994 |
| WO | WO 9422522 | 10/1994 |
| WO | WO-2004/056417 | 7/2004 |

* cited by examiner

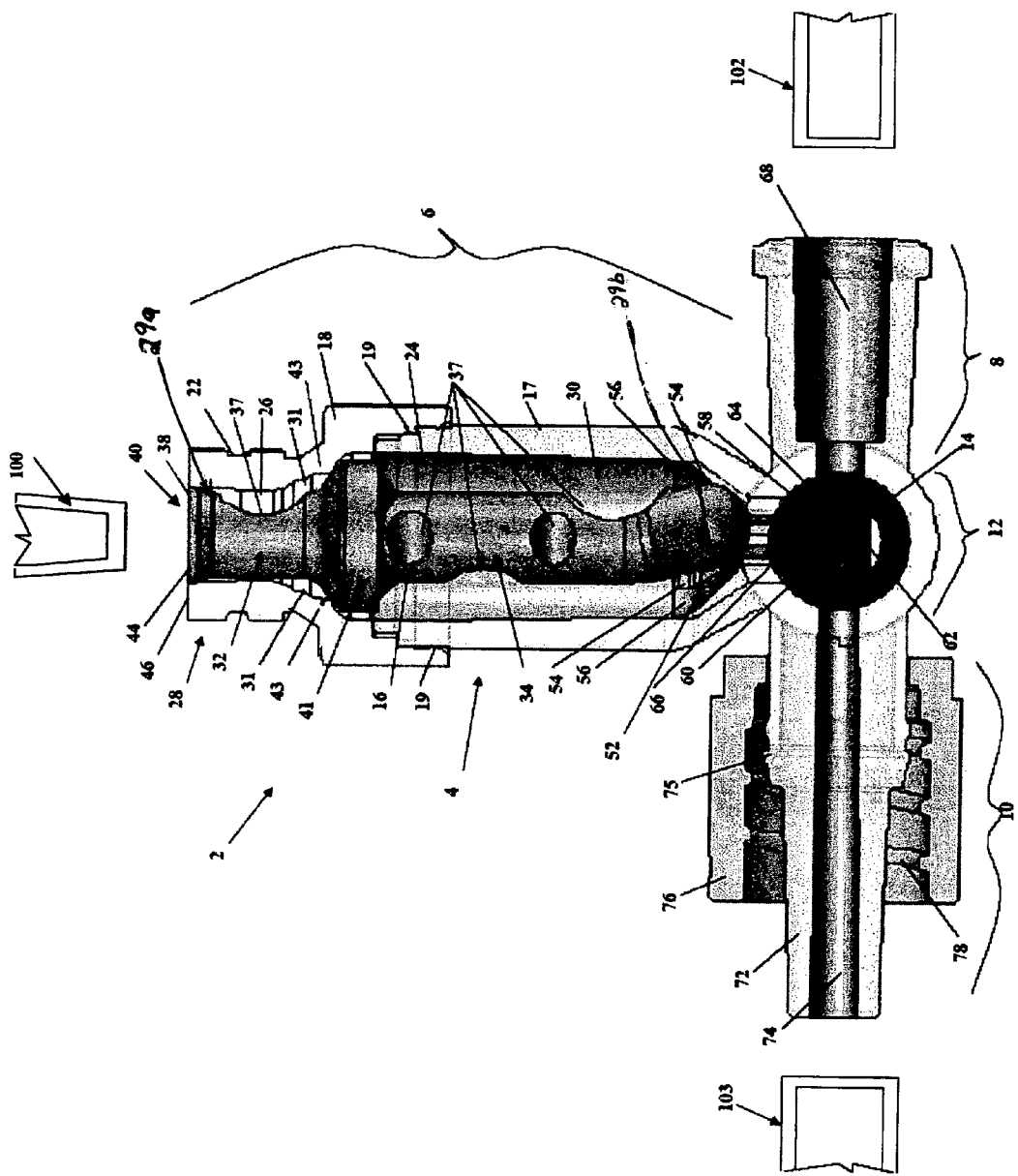

11

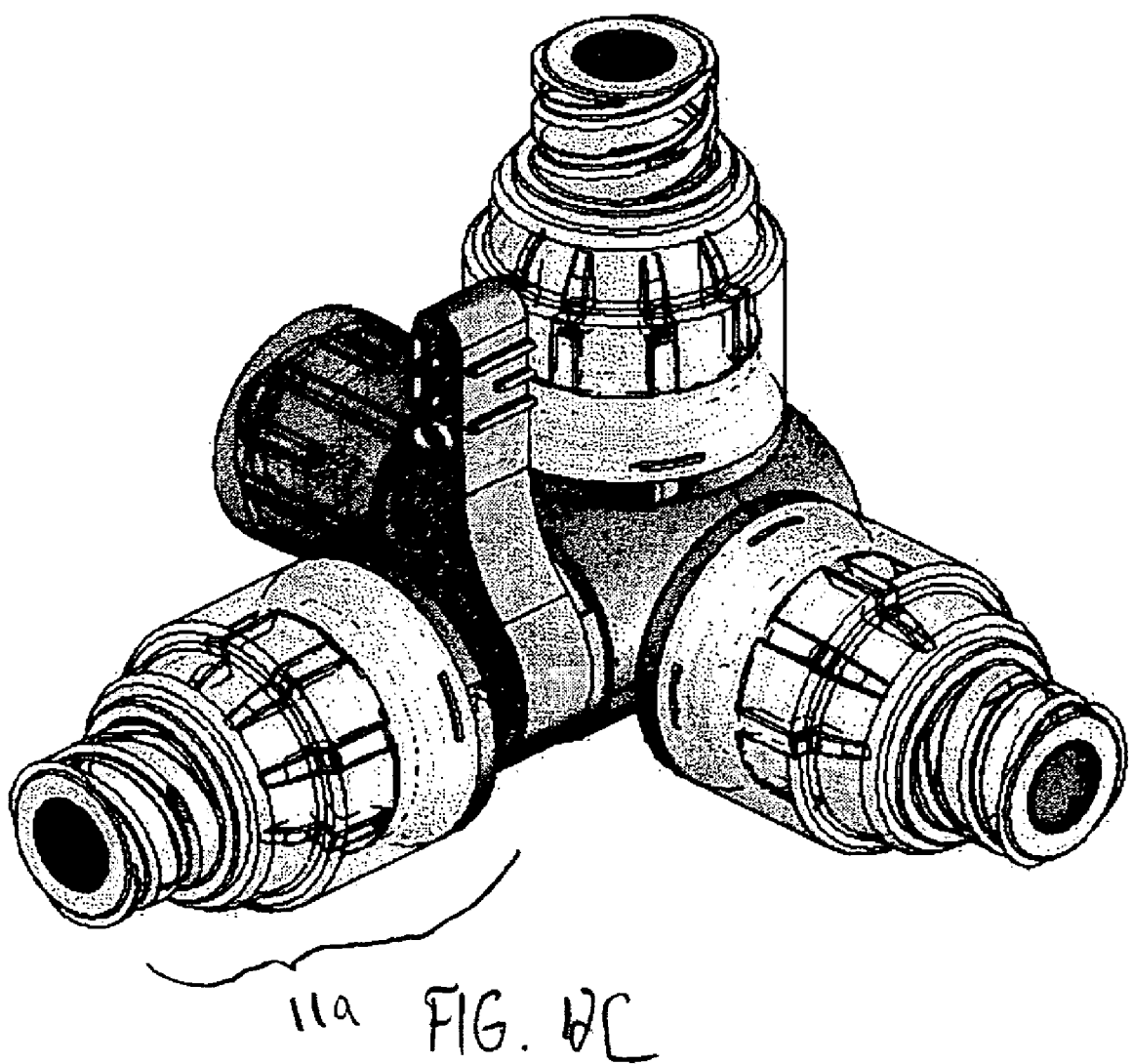
11a  FIG. 8C

FLUID CONTROL DEVICE WITH VALVE AND METHODS OF USE

FIELD OF THE INVENTION

The present invention is directed to a fluid control device and methods for transferring fluids and, in particular, a fluid control device for directing fluid flow, which incorporates a needleless access device.

BACKGROUND OF THE INVENTION

Connectors, such as stopcocks, have been used in intravenous systems to guide fluid flow between fluid transfer devices. In general, stopcocks comprise a housing with three or more ports. A moveable control device is positioned within the housing between the ports and is connected to a knob outside of the housing. The control device has several intersecting fluid flow channels therethrough which are angled with respect to each other. The angles between the fluid flow channels correspond to the angles between the ports. The knob is turned to align the fluid flow channels with two or more ports so that fluid may flow between the ports. The orientation of the control device may also prevent fluid from flowing between certain ports. For example, where a stopcock has three ports, the knob may be turned so that the control device allows fluid to flow between a first port and a second port but not between the first and second ports and a third port. In another orientation of the control device, fluid can flow between all three ports.

Needleless access devices are used to inject medications or other fluids into a patient or withdraw fluids from a patient. These devices form part of an intravenous system and have valves positioned therein. The valves are actuated by insertion of a fluid transfer device such as, for example, a male luer of a syringe into a first end of the device. A second end of the needleless access device is attached to a second fluid transfer device such as an intravenous tube or other connector. All injections/withdrawal of fluid can be made through the needleless access device. Thus, needleless access devices provide a safe and efficient way to repeatedly inject fluid into and/or withdraw fluid from intravenous systems. Moreover, needleless access devices eliminate the need to use traditional metal needles and prevent needle stick injuries and the possibility of transmitting blood born pathogens to healthcare professionals.

It is desirable to have a single device which incorporates both a stopcock and a needleless access device.

SUMMARY OF THE INVENTION

The present invention relates to a fluid control device for transferring fluids. In particular, the fluid control device may incorporate a needleless access device. The fluid control device may comprise a housing having a first port, a second port, a third port and a connecting portion for connecting the first, second and third ports to each other. A first valve element may be positioned in the first port. In another embodiment, a second valve element may be positioned in the second port and/or a third valve element may be positioned within the third port. Moreover, other embodiments may comprise more than three ports.

In one embodiment, the first port may have a longitudinal axis and the first valve element may have an axis. The first valve element may have a first position where the axis of the first valve element may be parallel, co-axial and/or aligned with the longitudinal axis of the first port, and a second position where the axis of the first valve element may be non-parallel and/or displaced from the longitudinal axis of the first port. Moreover, the first valve element may have a proximal end and a distal end. The proximal end may be closer to the distal end when the first valve element is in an opened position than when the first valve element is in a closed position.

The fluid control device may also have a fluid director, which may be moveable within the connecting portion. The fluid director may have one or more fluid passageways intersecting each other at angles so that fluid may flow through the passageways. The fluid director may be oriented within the connecting portion such that at least one fluid passageway may align with two or more ports. Thus, fluid may flow from one port through one or more fluid passageways and into at least one other port. To prevent fluid from leaking from the fluid control device, in one embodiment, the fluid director may be made of a soft material such that the fluid director may tightly fit within the connecting portion while still being able to move therein. In another embodiment, the fluid director may have a sleeve, which may be positioned between the fluid director and the connecting portion.

An actuation mechanism may be operably associated with the fluid director and may be used to orient the fluid director such that fluid may move, for example, between the first and second port, the first and third port, the second and third port, and/or the first, second and third ports. In some embodiments, the actuation mechanism may have a port passing therethrough such that fluid may flow through the actuation mechanism.

In one embodiment, the second and third ports may have an inner surface, an outer surface, a distal end proximate the connecting portion, and a proximal end opposite the distal end. At least one of the second and third ports may have at least one bonding medium reservoir. The bonding medium reservoir may be at least one recess in at least one of the inner surface and the outer surface of at least one of the second and third ports and may extend a length between the proximal end and the distal end of at least one of the second and third ports.

The present invention also relates to a method of transferring fluid. The first valve element may be moved between a first position, where fluid may be prevented from flowing past the first valve element, and a second position, where fluid may flow past the first valve element. The first valve element may be actuated by a first fluid transfer device. For example, upon insertion of the first fluid transfer device, the first valve element may move from the first position to the second position. And, when the fluid transfer device is removed from the first port, the first valve element may move from the second position to the first position. When the first valve element is in the second position, fluid may flow past the first valve element into at least one fluid passageway and through at least one of the second and third ports. Fluid may then flow out of the second and/or third port and into a second and/or third fluid transfer device, respectively. Alternatively, fluid may flow from the second and/or third ports through at least one fluid passageway and into the first port. Fluid may then flow past the first valve element and into the first fluid transfer device. An actuation mechanism may be used to move the fluid director and orient at least one fluid passageway so that fluid may flow between at least two ports.

In one embodiment, the method may comprise transferring fluid through at least one of the second and third ports in at least one of a first direction out of the fluid control device and a second direction into the fluid control device. The first valve element may cause movement of fluid through at least one of the second and third ports in the second direction in response to movement of the first valve element from a closed position to an opened position. Further, the first valve element may also cause movement of fluid through at least one of the second and third ports in the first direction in response to movement of the first valve element from the opened position to the closed position.

BRIEF DESCRIPTION OF THE DRAWINGS

The present invention can be better understood by reference to the following drawings, wherein like references numerals represent like elements. The drawings are merely exemplary to illustrate certain features that may be used singularly or in combination with other features and the present invention should not be limited to the embodiments shown.

FIG. 1B is a partial cross-sectional view of the device of FIG. 1A;

FIG. 12C is an alternative exemplary embodiment of the device of FIGS. 4A and 4B;

DETAILED DESCRIPTION

Figure 1A:
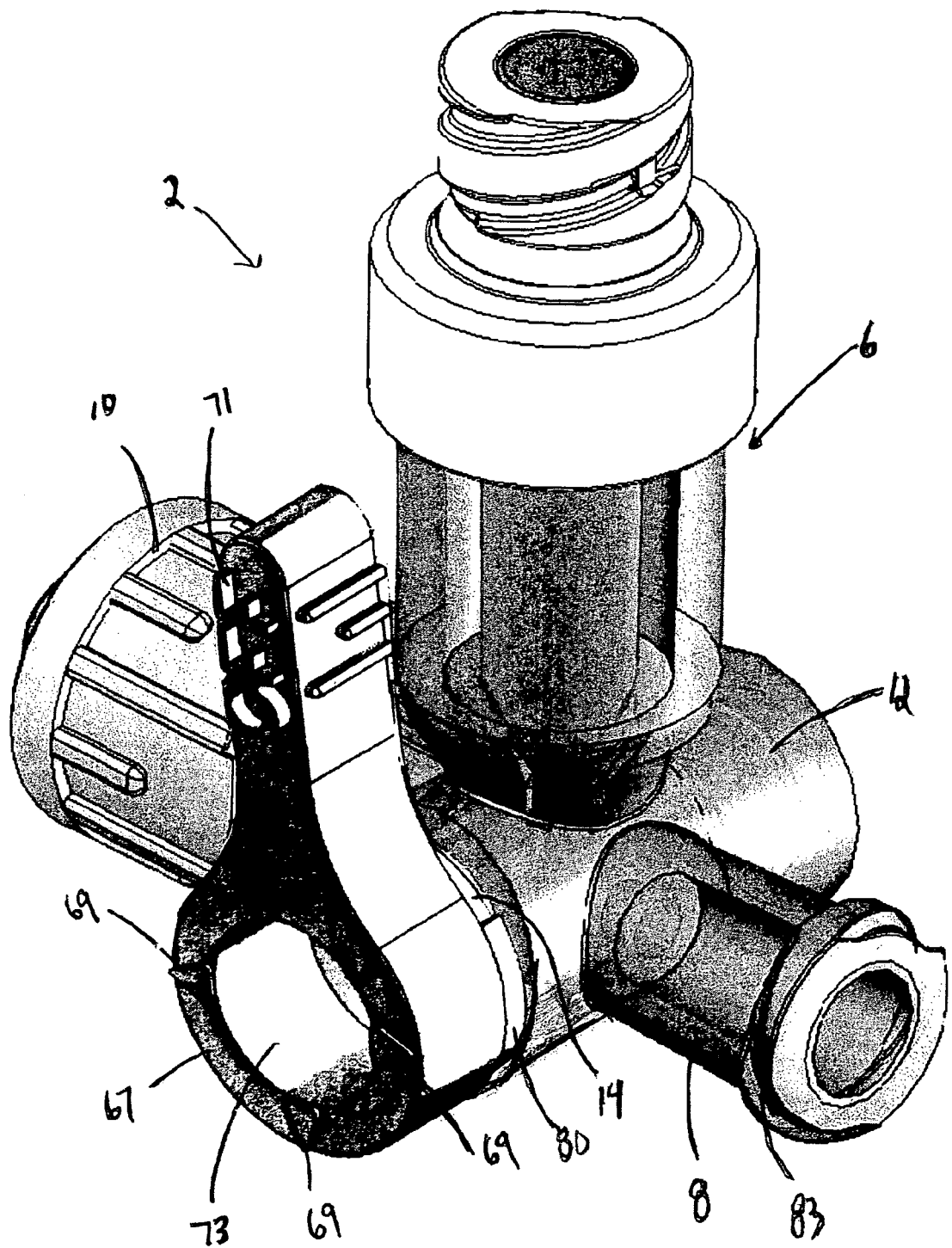
FIG. 1A is perspective view of an exemplary embodiment of the device of the present invention.

FIGS. 1A and 1B shows an exemplary embodiment of a fluid control device 2 for transferring fluid. The term "fluid" may include, for example, blood, medication, saline, water, oxygen or other gas, air (i.e, a mixture of gases).

Figure 2A:
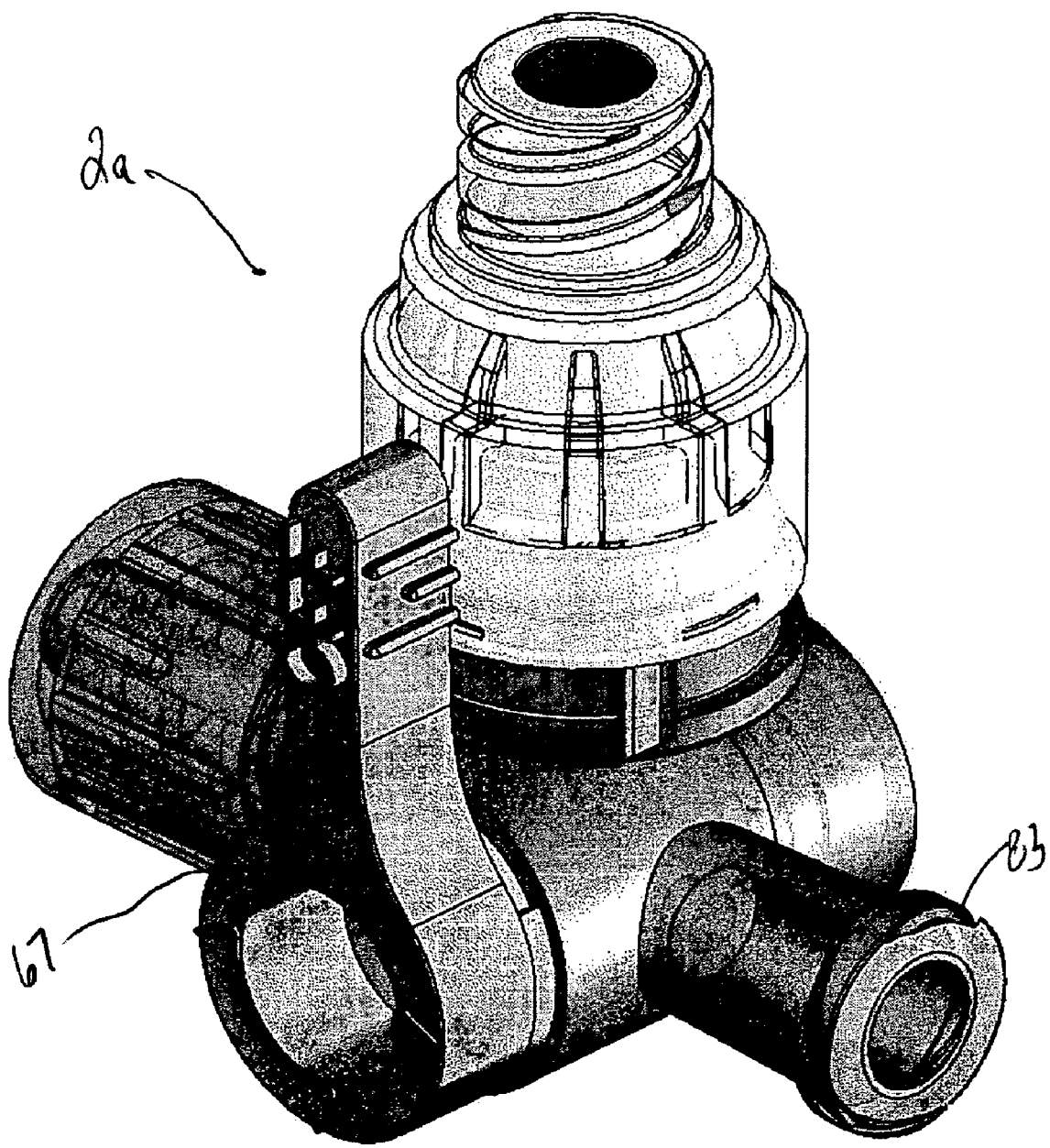
FIG. 2A is a perspective view of an alternative exemplary embodiment of the device of the present invention.
Figure 2B:
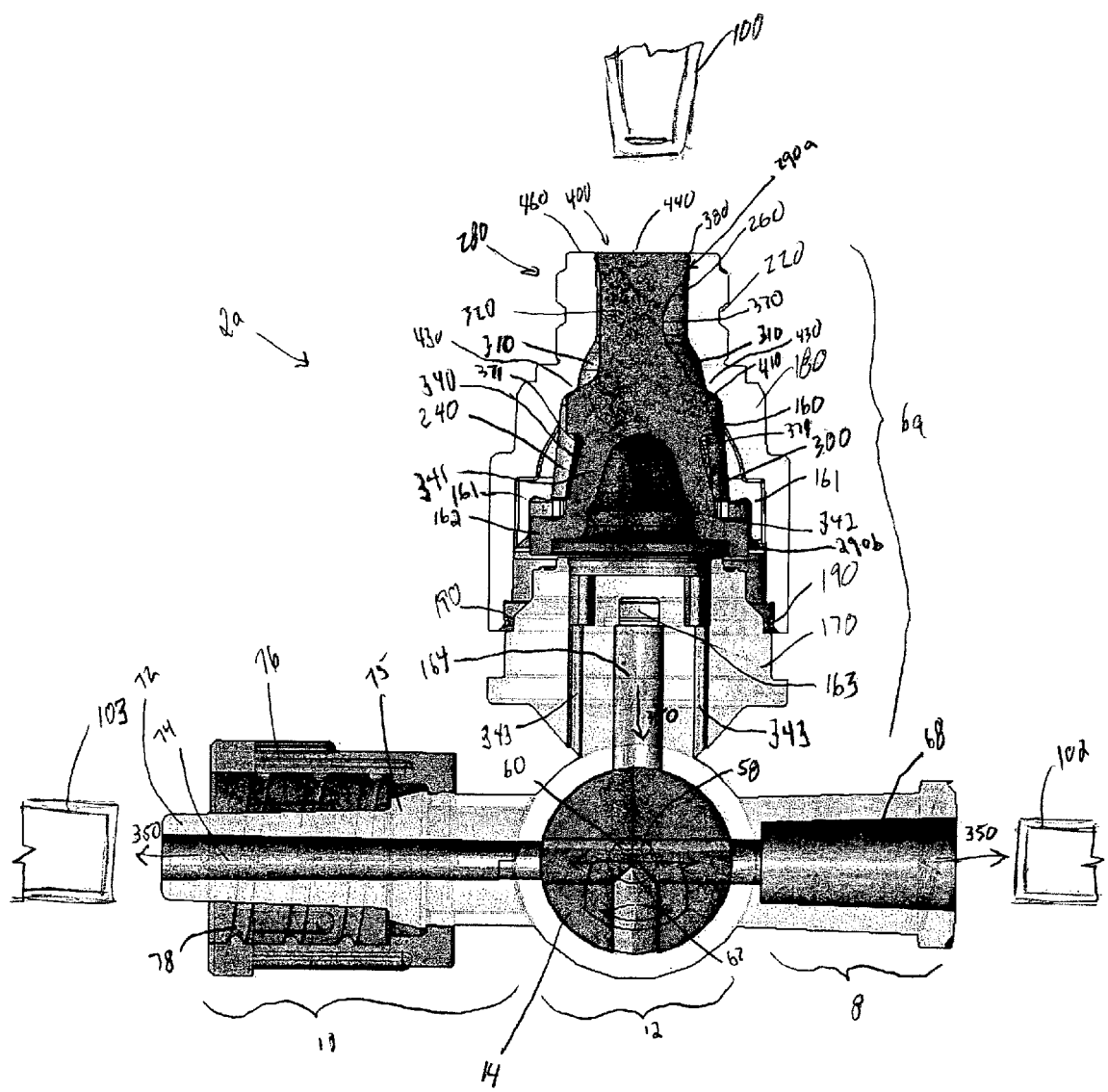
FIG. 2B is a cross-sectional view of the device of FIG. 2A.

The fluid control device 2 of the present invention may comprise a housing 4. The housing 4 may comprise a first port 6, a second port 8, a third port 10, and a connecting portion 12. A fluid director 14 may be positioned within the connection portion 12 and a first valve element 16 may be positioned within the first port 6. FIGS. 2A and 2B shows an alternative construction of the first port. As illustrated in FIGS. 2A and 2B, the fluid control device 2a may have a first valve element 160, which may be positioned within the first port 6a. It should, however, be understood that those of ordinary skill in the art will recognize many modifications and substitutions which may be made to various elements of the present invention.

The first port 6, 6a, second port 8, third port 10, connecting portion 12, and/or fluid director 14 may be made of, for example, metal, plastic (e.g., polycarbonate, acrylonitrile butadiene styrene (ABS)), a composite material (i.e., two or more materials) (e.g., copolyester), or rubber. Moreover, the first port 6, 6a, second port 8, third port 10, connecting portion 12, and/or fluid director 14 may be made of the same or different materials and may be transparent or opaque. Various factors may be considered when determining the material to be used for the first port 6, 6a, second port 8, third port 10, connecting portion 12, and/or fluid director 14, including compatibility with fluids flowing through the fluid control device 2, 2a (i.e., material does not chemically and/or physically react with fluids flowing through the fluid control device 2, 2a) (e.g., lipid resistance), the ability to withstand sterilization/cleaning (i.e., cleaning products used in sterilization), weight, durability, mechanical strength, resistance to bacterial formation, ease and cost of manufacturing, and ability to be attached to other materials. And, while the first port 6, 6a, second port 8, third port 10, connecting portion 12, and fluid director 14 are shown as cylindrical, the first port 6, 6a, second port 8, third port 10, connecting portion 12, and/or fluid director 14 may be any shape (e.g., polygonal). Various factor may be considered when determining the shape of the first port 6, 6a, second port 8 and third port 10, including the compatibility with standard fluid transfer devices (e.g., an intravenous tube, syringe, catheter or other connector), the desired path of fluid flow, ability of the fluid control device 2, 2a to be flushed, and clearance around internal components (e.g., the first valve element 16, 160). With regard to the connecting portion 12 and the fluid director 14, their shape may be a factor of, for example, the ability of the fluid director 14 to be moved within the connecting portion 12.

Additionally, the first port 6, 6a, second port 8, third port 10 and/or connecting portion 12 may be made, for example, by injection molding, extrusion, casting, compression molding or transfer molding and may be constructed as a single piece or may be separate pieces attached together by, for example, bonding medium (e.g., adhesive), threads, ultrasonic welding, ultraviolet curing, tape, corresponding clip and clip engaging portion(s) (e.g., a snap connection), spin welding or otherwise melting together. In another embodiment, the first port 6, 6a, second port 8, third port 10, and/or connecting portion 12 may be separate pieces attached together either permanently or removeably by any of the attachment means described above. Moreover, a washer (not shown) (e.g., an O-ring) may be positioned between the first port 6, 6a, second port 8, third port 10, and/or connecting portion 12 to prevent fluid from leaking out of fluid control device 2, 2a.

Alternatively, the fluid control device 2, 2a may be molded or otherwise formed, for example, in two halves, which may be joined together by any of the means described above. In one embodiment, the first port 6, 6a, second port 8, third port 10, and connecting portion 12 may be joined using one or more hinges (not shown). In general, a separate piece construction may allow for insertion/replacement of parts within the fluid control device 2, 2a (e.g., the fluid director 14, the first valve element 16, 160) and/or cleaning the inside of fluid control device 2, 2a.

As shown in FIG. 1B, the first port 6 may comprise a base portion 17 and a cap 18. And, as illustrate in FIG. 2B, the first port 6a may comprise a base portion 170 and a cap 180. The base portion 17, 170 and cap 18, 180 may be integral or two separate pieces, which may be connected by, for example, bonding medium (e.g., adhesive), threads, ultrasonic welding, ultraviolet curing, tape, corresponding clip and clip engaging portion(s) (e.g., a snap connection), spin welding or otherwise melting together. In one embodiment, the base portion 17, 170 may have external threads (not shown) on external portion 19, 190 to engage internal threads (not shown) of the cap 18, 180. In addition, the cap 18, 180 may have an external threaded portion 22, 220 (or an internal threaded portion (not shown)) to engage a corresponding threaded portion of a first fluid transfer device 100. All means for attaching a first fluid transfer device 100 to the first port 6, 6a, however, are envisioned (e.g., clip and a corresponding clip engaging portion(s), tape, friction, etc.). Such a design may allow for the first fluid transfer device 100 to be held securely onto the first port 6, 6a when fluid is transferred between the first fluid transfer device 100 and the first port 6, 6a.

Further, the base portion 17, 170 and cap 18, 180 may define a channel 24, 240. The channel 24, 240 may, in turn, comprise a proximal channel 26, 260 located at a proximal end 28, 280 and a main channel 30, 300. The inner surface of the channel 24, 240 may be smooth or may have, for example, grooves, slots, protrusions, ridges or ribs. For example, as illustrated in FIG. 2B, the main channel 300 may have ribs 161, which may have fluid channels therebetween. Moreover, one or more fluid paths 31, 310 may be provided in the cap 18, 180. The fluid paths 31, 310 may be one or more individual longitudinal channels or, as illustrated in FIGS. 1B and 2B, a widened diameter portion around the entire inner surface of the proximal channel 26, 260. Such internal structures may be provided, for example, to guide the flow of fluid past the first valve element 16, 160. It should be noted that the term "flow past" or any similar term using the word "past" or "pass" may mean fluid flows through or around any structure in the fluid control device 2, 2a including any portion or the entirety of the first valve element 16, 160.

Figure 3A:
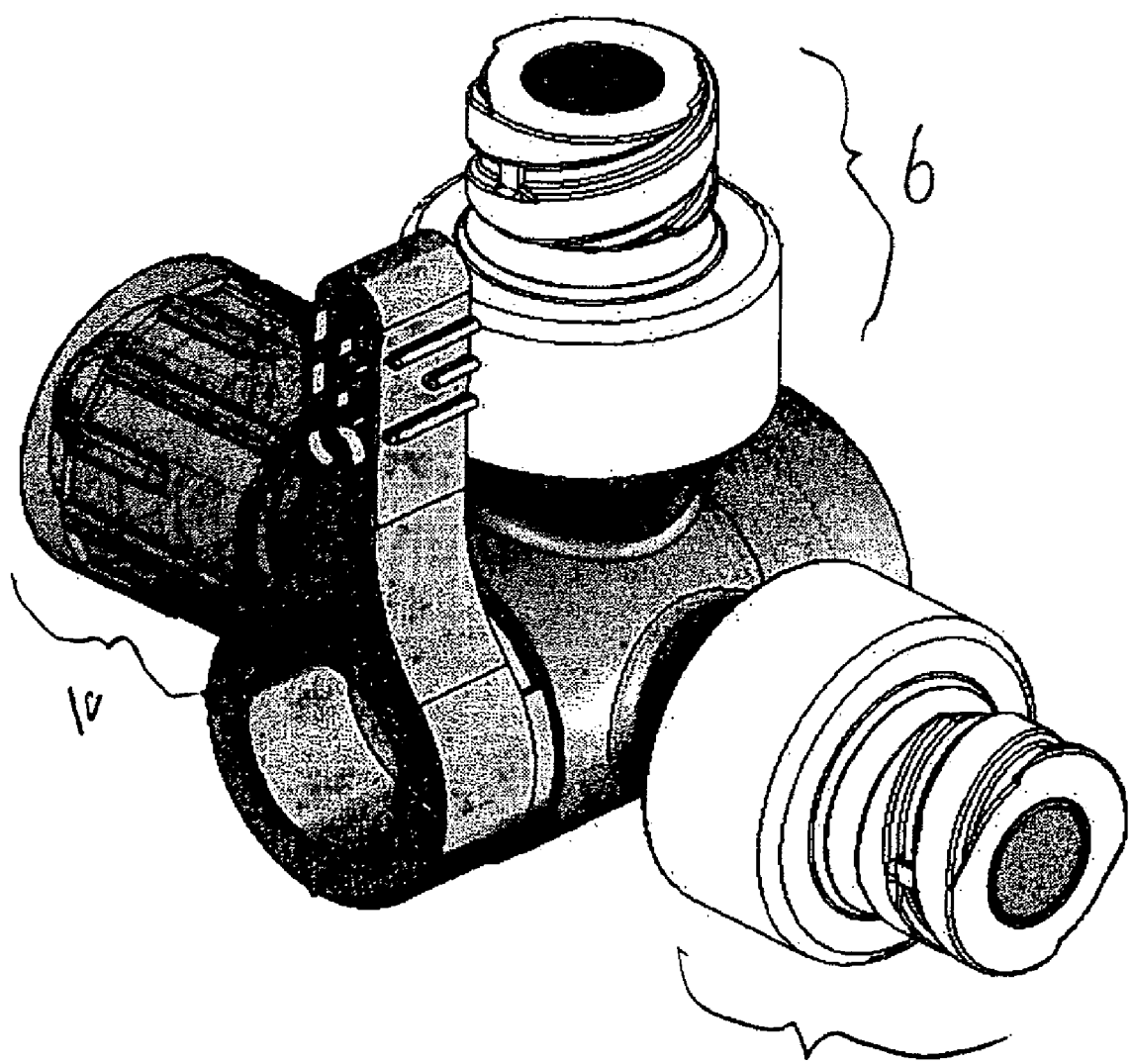
FIG. 3A is a perspective view of an alternative exemplary embodiment of the device of FIGS. 1A and 1B.
Figure 3B:
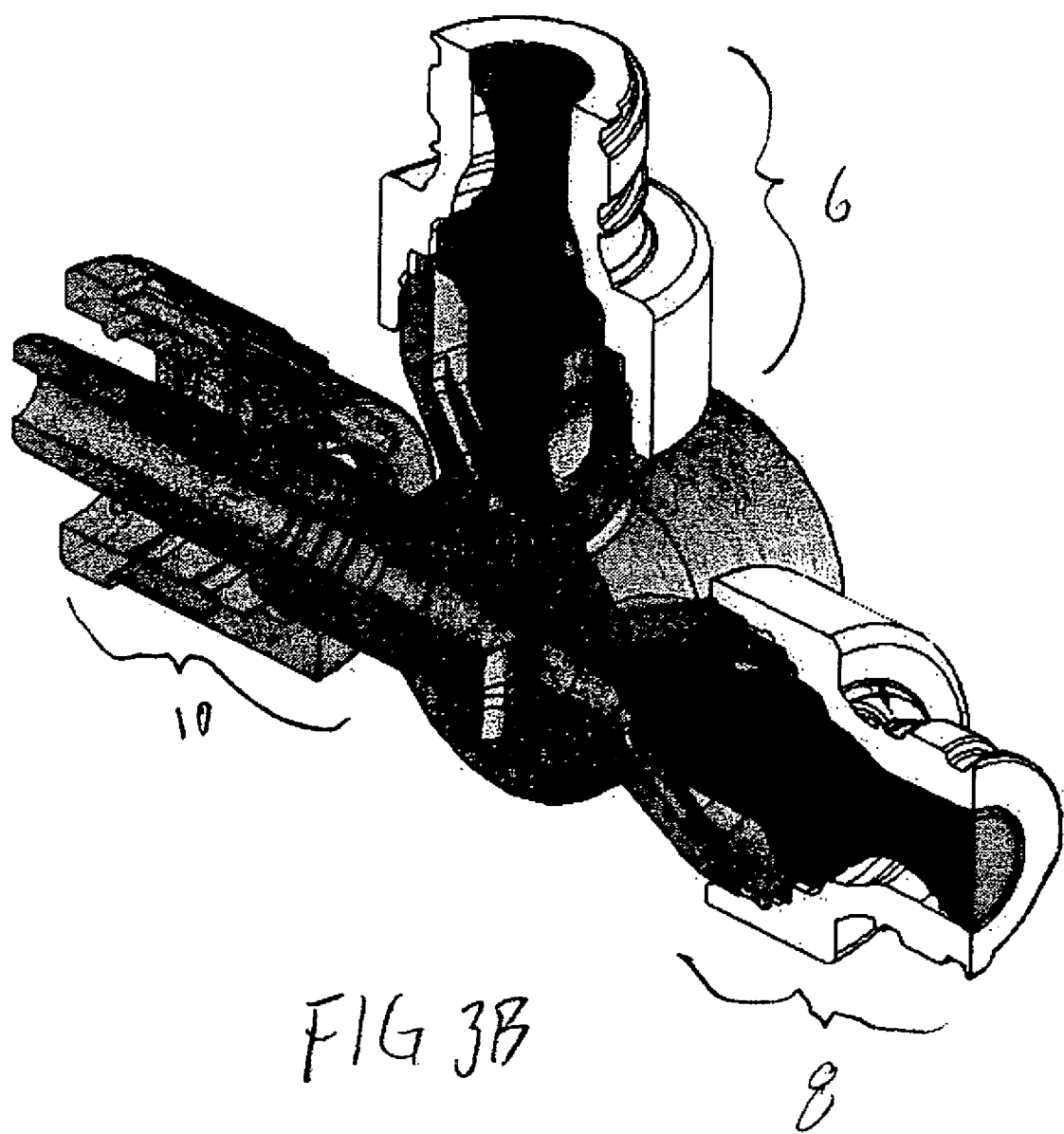
FIG. 3B is a cross-sectional view of the device of FIG. 3A.
Figure 4A:
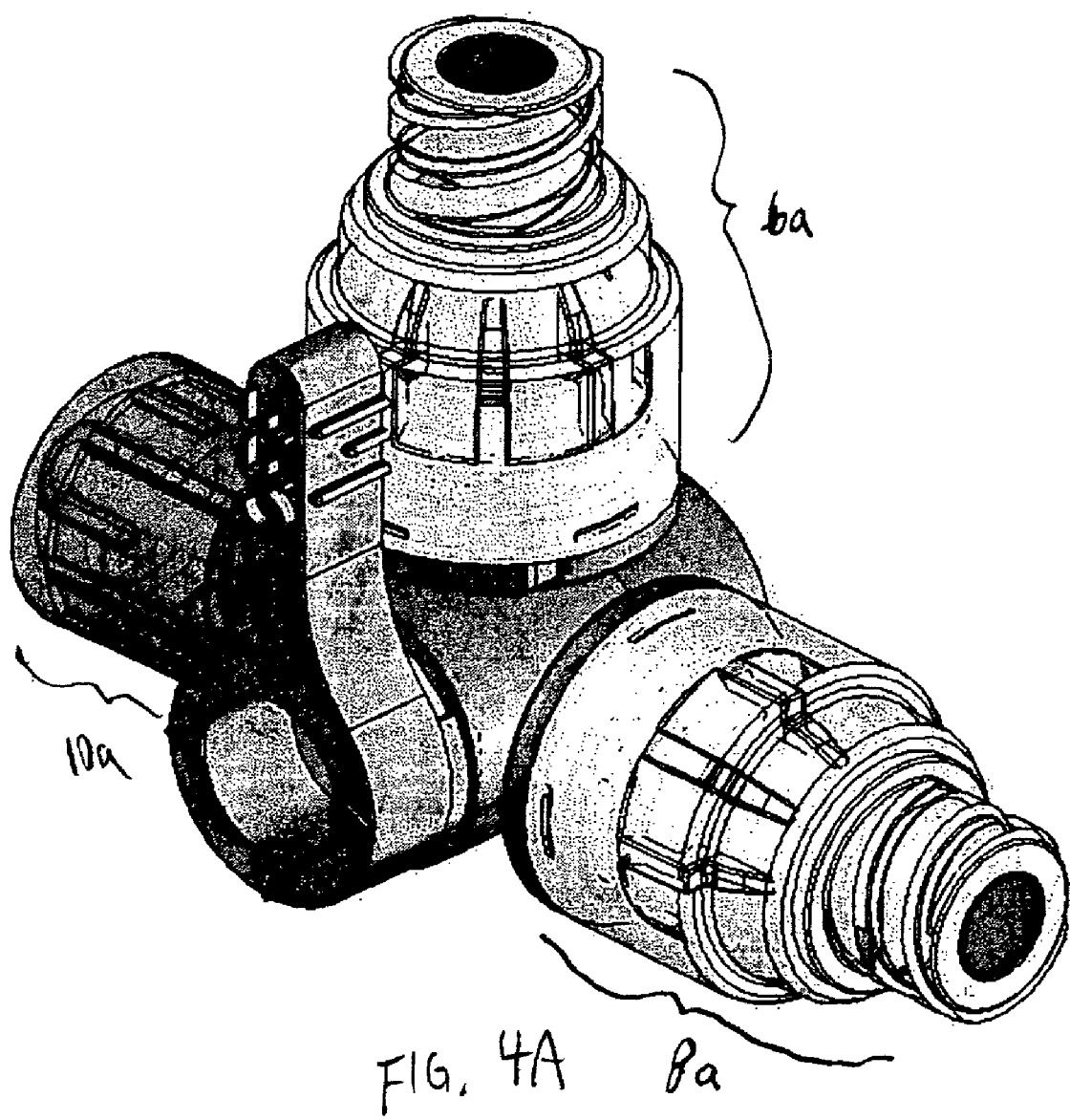
FIG. 4A is a perspective view of an alternative exemplary embodiment of the device of FIGS. 2A and 2B.
Figure 4B:
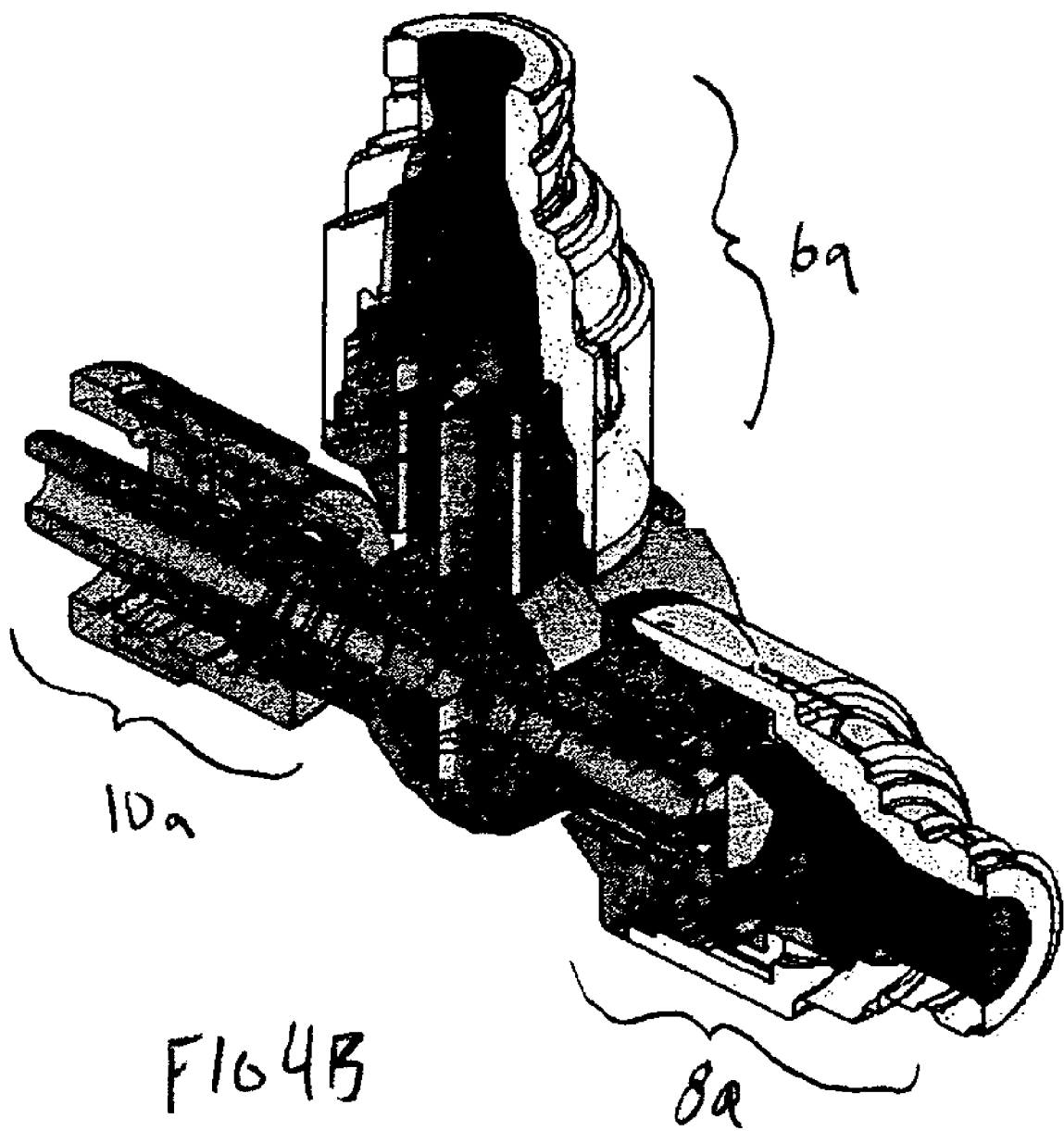
FIG. 4B is a cross-sectional view of the device of FIG. 4A.

The first valve element 16, 160 may be positioned within first port 6, 6a. It should be noted that a valve similar or identical to the first valve element 16, 160 may be positioned in more than one port and/or different valve elements may be positioned in each port such that each port may be a different type of needleless access device. For example, FIGS. 3A and 3B illustrate an alternative embodiment of FIGS. 1A and 1B where the second port 8 may have the same construction as the first port 6, and FIGS. 4A and 4B illustrate an alternative embodiment of FIGS. 2A and 2B where the second port 8a may have the same construction as the first port 6a. Thus, the fluid control device 2, 2a may have a second valve element. In other embodiments, the third port 10, 10a may have the same construction as the first port 6, 6a or second port 8, 8a of FIGS. 3A and 4A. The fluid control device 2, 2a may therefore have a third valve element. In other embodiments, the fluid control device 2 may have a second port 8 which may be similar or identical to port 8a, or the fluid control device 2a may a second port 8 which may be similar or identical to port 6.

Figure 5:
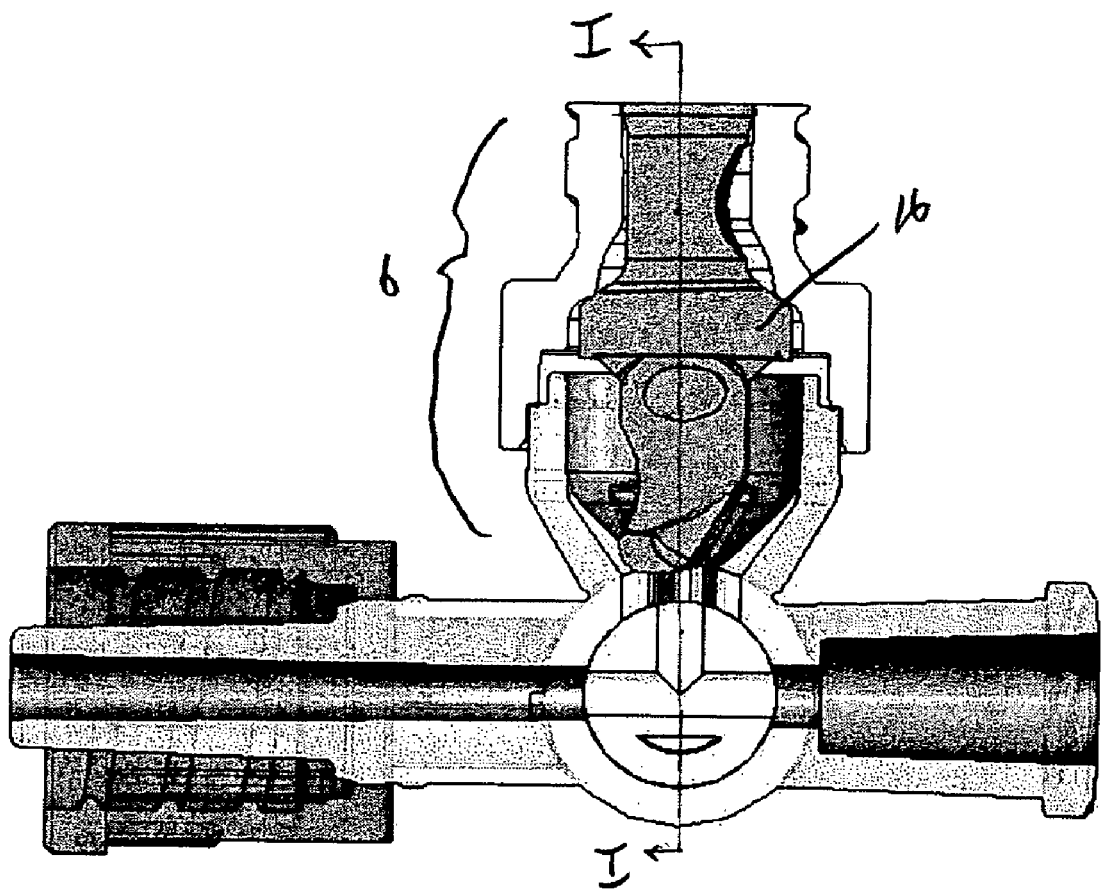
FIG. 5 is a partial cross-sectional view of an alternative exemplary embodiment of the device of FIGS. 1A and 1B.

In one embodiment of FIG. 1B, the first valve element 16 may have a length, from the top 44 of the first valve element 16 to the distal most portion of distal end 29b, between about 0.15 inches and about 1.5 inches, more preferably, between about 0.25 inches and about 1.0 inch and, most preferably, between about 0.4 inches and about 0.6 inches. Moreover, in one embodiment of FIG. 2B, the first valve element 160 may have a length, from the top 440 of the first valve element 160 to the distal most portion of distal end 290b, between about 0.3 inches and about 1.5 inches, more preferably, between about 0.4 inches and about 1.2 inches and, most preferably, between about 0.55 inches and about 0.75 inches. As the length of the first valve element 16, 160 changes, the size of the first port 6, 6a may also change. As illustrated by a comparison of FIG. 1B and FIG. 5, with a decrease in the size of the first valve element 16, the size of the first port 6 may also proportionately decrease. Moreover, as will be appreciated by those skilled in the art, decreasing the size of the first port 6, 6a (e.g., from the size shown in FIG. 1B to the size of FIG. 5) may provide advantages, including reducing the priming volume (which may be beneficial to children and the elderly), increasing the efficiency of fluid delivery, and/or minimizing the flushing volume such that a patient may receive a full dose of fluid (e.g., medication, saline).

As shown in FIGS. 1B and 2B, the first valve element 16, 160 may comprise a head portion 32, 320 and a body portion 34, 340. The head portion 32, 320 and the body portion 34, 340 may be one integral piece or separate pieces and may be made of a solid piece of material. In other embodiments, the head portion 32, 320 and/or body portion 34, 340 may be hollow. For example, as shown in FIG. 2B, the head portion 320 may be made of a solid piece of material and the body portion 340 may be hollow. In an embodiment where the head portion 32, 320 and/or body portion 34, 340 may be hollow, there may be one or more openings (not shown) in the head portion 32, 320 and/or body portion 34, 340. Fluid may be able to flow through the opening(s) and into and/or out of the head portion 32, 320 and/or body portion 34, 340.

As shown in FIG. 2B, the body portion 340 may have a wall 341 defining an internal chamber 342, which may contain fluid (e.g., air). The wall 341 may be solid (i.e., there may be no holes or openings therethrough). As will be discussed in further detail below with regard to the use of the fluid control device 2a, such a construction may provide significant advantages when the air contained inside the internal chamber 342 may flow in and out of the fluid control device 2a through one or more venting channels 343, which may be in communication with the chamber 342 and which may communicate with the outside of the fluid control device 2a.

Furthermore, the head portion 32, 320 and body portion 34, 340 may be made of the same or different materials such as, for example, plastic, a foam material, a composite material (i.e, made of two or more materials), a combination material (i.e., one material contained within another material) (e.g., a gel such as a hydrogel contained within rubber) or rubber (e.g., silicon polyisoprene) and may be transparent or opaque. The material may be elastomeric (i.e., compressible, stretchable, bendable, flexible, foldable or otherwise contortable). Various factors may be considered when determining the material to be used for the head portion 32, 320 and body portion 34, 340, including compatibility with fluids flowing through the fluid control device 2, 2a (i.e., the material does not react with fluids flowing through the fluid control device 2, 2a) (e.g., lipid resistance), the ability to withstand sterilization/cleaning (i.e., cleaning products used in sterilization), weight, durability, resistance to bacterial formation, ease and cost of manufacturing, ability to be attached to other materials, and mechanical properties (e.g., strength, resiliency; ability to be compressed, twisted, bended, folded, or otherwise contorted). Moreover, the head portion 32, 320 and body portion 34, 340 may be formed, for example, by injection molding (e.g., liquid injection molding), casting, or extrusion and may be any shape (e.g. polygonal or spherical head; polygonal or cylindrical body).

In embodiments where the head portion 32, 320 and body portion 34, 340 may be made of separate pieces, the head portion 32, 320 and body portion 34, 340 may be connected, for example, by a bonding medium (e.g., adhesive), threads, ultrasonic welding, ultraviolet curing, spin welding or otherwise melting together.

The first valve element 16, 160 may also comprise one or more grooves, recesses, notches (e.g., notches 37, 370) which may be located in the head portion 32, 320 and/or the body portion 34, 340 or both. As shown in FIG. 2B, the body portion 340 may also comprise one or more undercuts 371. Further, notches 37, 370 and/or undercuts 371 may be located anywhere on the outer surface of the head portion 32, 320 and/or body portion 34, 340. And where the head portion 32, 320 and/or body portion 34, 340 may be hollow, or have a wall, notches 37, 370 may be located anywhere on an inner surface of the head portion 32, 320 and/or body portion 34, 340.

The notches 37, 370 and/or undercuts 371 may facilitate compression, bending, canting, folding, and/or contorting of the first valve element 16, 160. In addition, compression, bending, canting, folding, and/or contorting may also be facilitated by the head portion 32, 320 and/or body portion 34, 340 being molded in a pre-cant position (such as shown in body portion 34 of FIG. 1B). Moreover, the notches 37, 370 and/or undercuts 371 may assist in guiding fluid flow through the first port 6, 6a for example, when the valve element 16, 160 may be in a compressed, bent, canted, folded, and/or contorted position. The notches 37, 370 may be any shape (e.g., round, elliptical, square, rectangular or polygonal), size, and may cover any amount of area of the head portion 32, 320 and/or body portion 34, 340. As shown in the embodiment of FIG. 1B, notches 37 may be smile cuts along a portion of the outer area of both the head and body portions 32, 34. And, as shown in FIG. 2B, notch 370 may be a smile cut in the head portion 320.

Additionally, the head portion 32, 320 may comprise a first enlarged portion 38, 380 at a proximal end 29a, 290a of the first valve element 16, 160 that may seal opening portion 40, 400. The head portion 32, 320 may also have a second enlarged portion 41, 410 which may engage a shoulder portion 43, 430 of the cap 18, 180. It will be appreciated by those skilled in the art that the second enlarged portion 41, 410 may engage any portion of the base portion 17, 170 and/or cap 18, 180. The enlarged portions 38, 380 and/or 41, 410 may prevent fluid from flowing past the first valve element 16, 160.

A top 44, 440 of the first valve element 16, 160 may be substantially flush with respect to the top 46, 460 of the cap 18, 180. Such a construction may allow for antiseptic swabbing of the tops 44, 440 and 46, 460. In another embodiment, not shown, the top 44, 440 of the first valve element 16, 160 may protrude out of the cap 18, 180 or may be sunken into the cap 18, 180. These constructions may also allow for antiseptic swabbing. Where top 44, 440 of the first valve element 16, 160 may be sunken into cap 18, 180 the top 44, 440 may be below the level of the top 46, 460 of the cap 18, 180. Additionally, the top 44, 440 of the first valve element 16, 160 may be flat or may have protrusions (not shown) extending therefrom. The protrusions may help guide fluid flow past the first valve element 16, 160.

The body portion 34, 340 may bias the head portion 32, 320 into the proximal channel 26, 260. It should be understood by those skilled in the art that the body portion 34, 340 may be any structure (e.g., a spring (not shown)) which may bias the head portion 32, 320 into the proximal channel 26, 260. In one embodiment of FIG. 1B, where the body portion 34 may be a solid piece of material, a spring (not shown) may be positioned around the body portion 34 of the first valve element 16. The spring may be held, for example, between the enlarged portion 41 and the housing 4—including the wall of the housing 4 and any portion connected/connectable to or integral with the housing 4 (e.g., the valve support 52 (discussed below)). In another embodiments, a spring may be positioned below the first valve element 16 (i.e., between the body portion 34 and the housing 4). In any embodiment, the body portion 34, 340 may be fixed or rest freely inside the fluid control device 2, 2a.

For example, as shown in FIG. 2B, the first valve element 160 may have an circular flange 162. The circular flange 162 may be captured between the base portion 170 and the cap 180. In particular, the circular flange 162 may be captured between the base portion 170 and one or more ribs 161 of the cap 180. In an alternative embodiment, the first valve element 160 may have one or more flange portions. In yet another embodiment of FIG. 2B, the first valve element 160 may be connected to the base portion 170, for example, by a bonding medium (e.g., adhesive), threads, ultrasonic welding, ultraviolet curing, spin welding or otherwise melting together. Such constructions may fix the valve element 160 within the fluid control device 2a.

Alternatively, as shown in FIG. 1B, the body portion 34 may freely rest on a valve support 52. In another embodiment, the body portion 34 may be fixed to the valve support 52 and/or within the fluid control device 2. As shown in FIG. 1B, the valve support 52 may be positioned in the channel 24 of the first port 6. The valve support 52 may support the first valve element 16 and may comprise one or more holding ribs 54. The holding ribs 54 may be straight or may have a concave shape or any other shape. One or more fluid flow channels 56 may be located between holding ribs 54. The fluid flow channels 56 may enable fluid to flow past the first valve element 16. It should be noted, however, that the valve support 52 may be any structure located anywhere within the first port 6, so long as the valve support 52 supports the first valve element 16 and allows fluid to flow past the first valve element 16.

Further, the holding ribs 54 may be made of metal, plastic (e.g., polycarbonate, acrylonitrile butadiene styrene (ABS)), a composite material (i.e., two or more materials) (e.g., copolyester), or rubber (e.g., polyisoprene) and may be transparent or opaque. The holding ribs 54 may be made of the same or different materials as the housing 4. Various factors may be considered when determining the material to be used for the holding ribs 54 including, compatibility with fluids flowing through the fluid control device 2 (i.e., material does not chemically and/or physically react with fluids flowing through the fluid control device 2) (e.g., lipid resistance), the ability to withstand sterilization/cleaning (i.e., cleaning products used in sterilization), weight, durability, mechanical strength, resistance to bacterial formation, ease and cost of manufacturing, and ability to be attached to other materials.

Additionally, the holding ribs 54 may be integral with the surface of the channel 30 or may be separate from the channel 30. If a separate piece, the holding ribs 54 may be connected to the channel 30 by, for example, a bonding medium, threads, ultrasonic welding, ultraviolet curing, spin welding or otherwise melting together. And, if the housing 4 is designed to allow access therein, the holding ribs 54 may be replaceable.

Turning now to the interconnection between ports, the first port 6, 6a may be connected to the second port 8 and/or the third port 10 by a connecting portion 12. The first port 6, 6a, second port 8 and/or third port 10 may be integral with the connection portion 12 or may be attachable to the connecting portion 12. Furthermore, the first port 6, 6a and the second port 8 may be at an angle 58 with respect to each other. The first port 6, 6a and the third port 10 may be at an angle 60 with respect to each other. And, the second port 8 and the third port 10 may be at an angle 62 with respect to each other. The angles 58, 60 and 62 may be, for example, between about 30 degrees and about 180 degrees. More preferably, angles 58 and 60 may be, for example, between about 55 degrees and about 135 degrees and, more preferably, between about 80 degrees and about 100 degrees. Further, angle 62 may be, for example, about 180 degrees. The angle chosen may be a consideration of various factors, including ease of injection/withdrawal of fluid, weight of the fluid control device 2, 2a in a natural hanging position, and prevention of tube kinking. It will be appreciated by those skilled in the art that additional port(s) may also be incorporate into the fluid control device 2, 2a (e.g., FIGS. 12A through 12D). In an embodiment with additional port(s), the additional port(s) may be at an angle, such as those described above, with any of the first port 6, 6a, second port 8 and/or third port 10.

Figure 6:
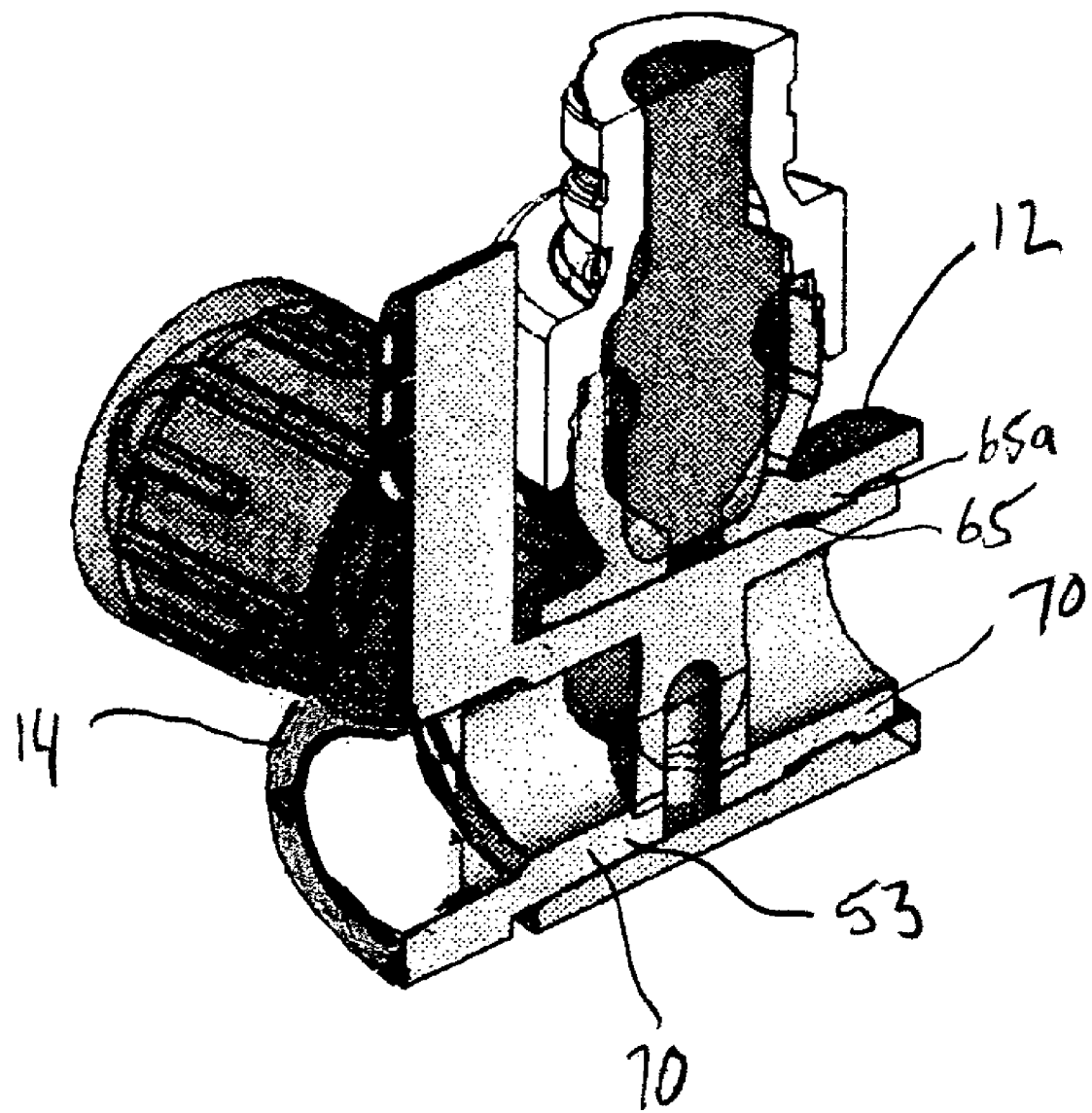
FIG. 6 is a cross-sectional view of the device of FIG. 5 along I-I.
Figure 7:
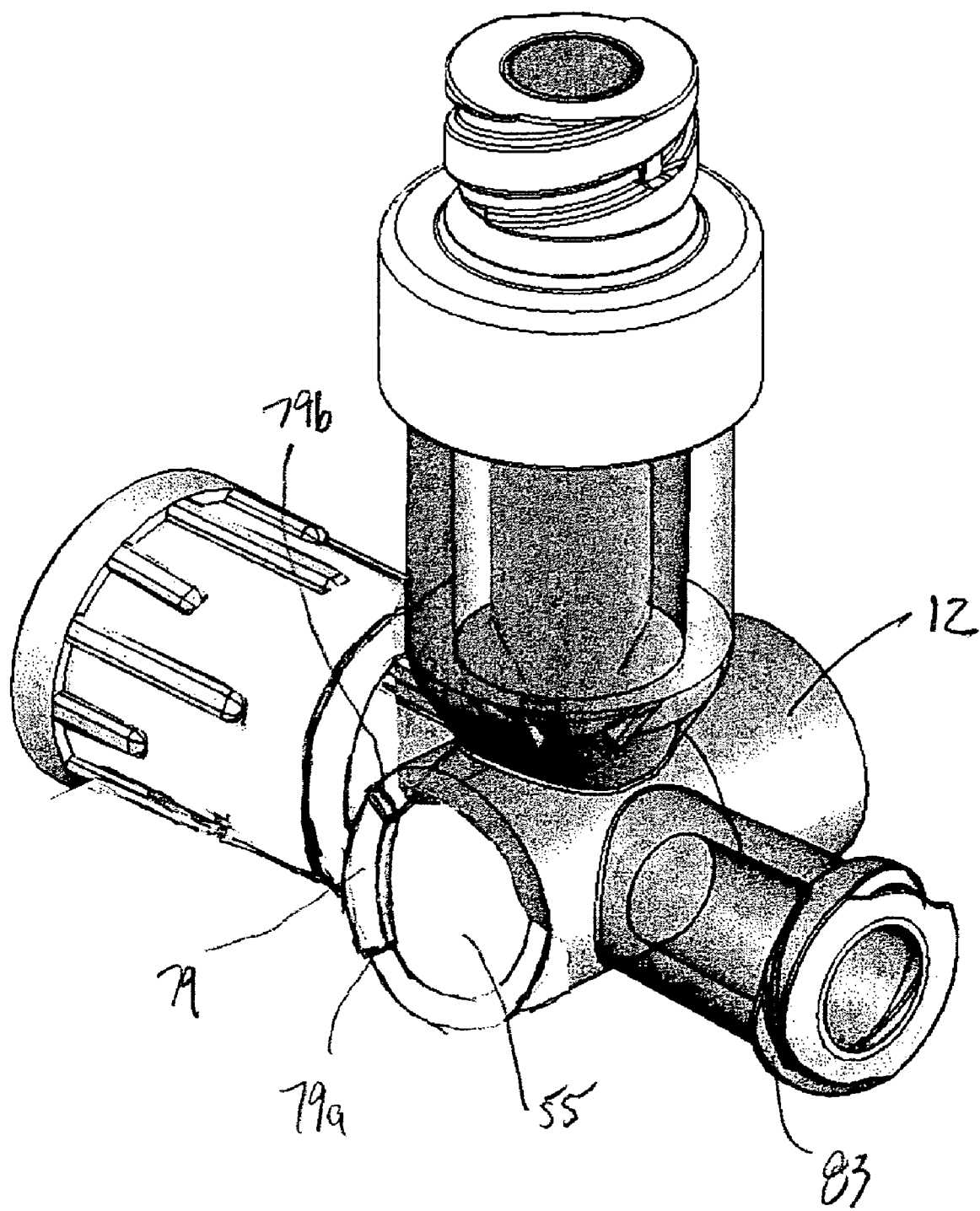
FIG. 7 is a perspective view of the device of FIGS. 1A and 1B without a fluid director.
Figure 8:
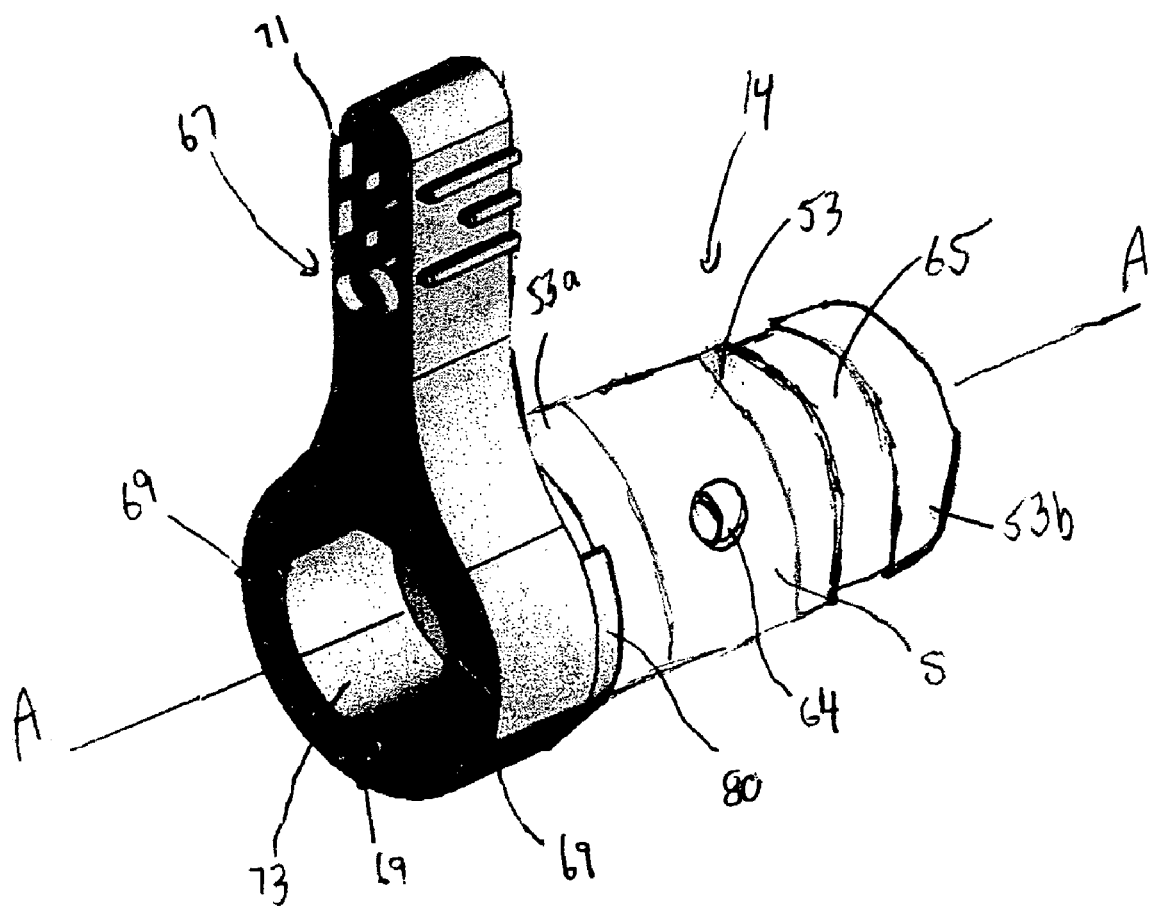
FIG. 8 is a perspective view of an exemplary embodiment of a fluid director.
Figure 9:
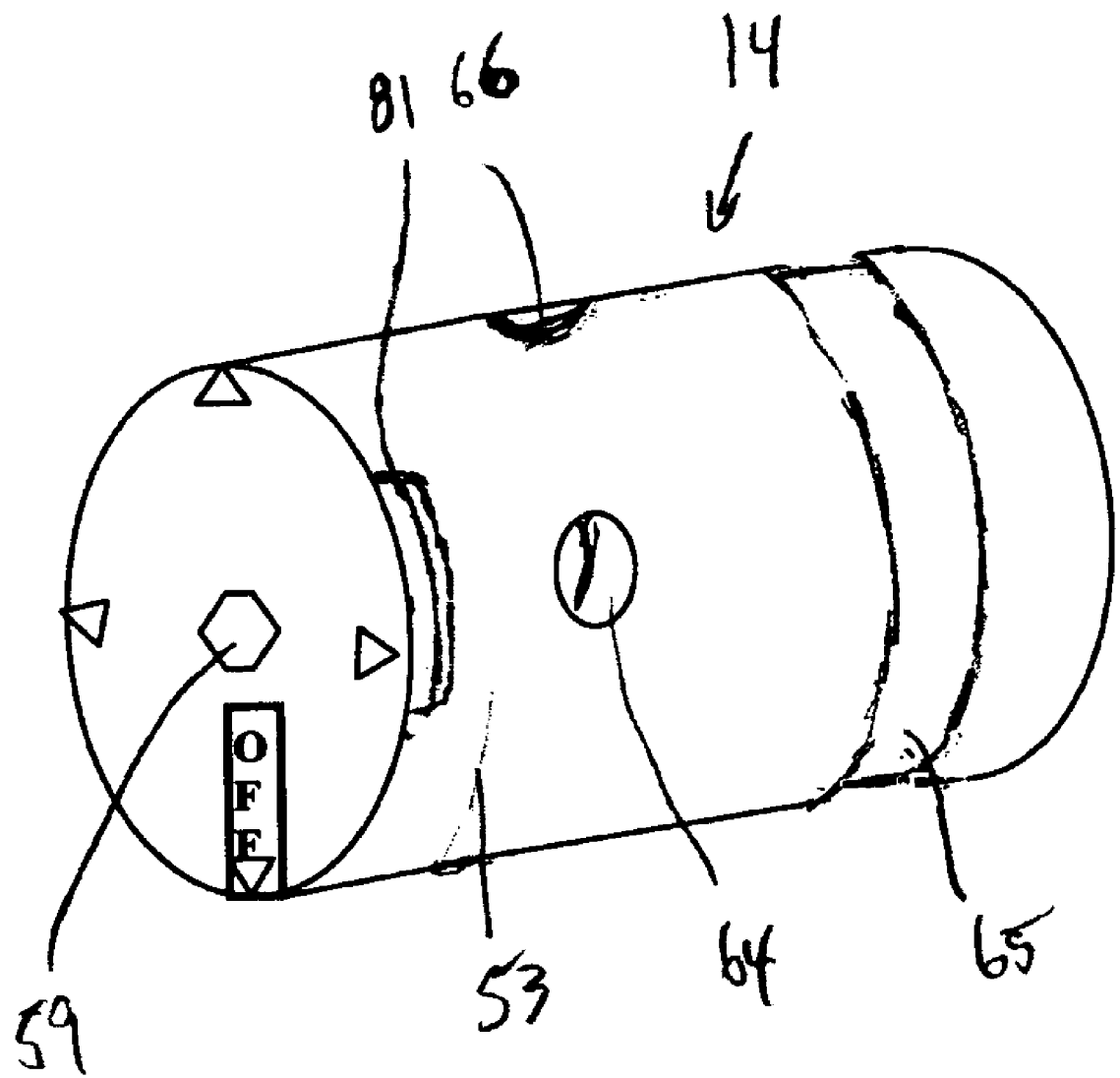
FIG. 9 is a perspective view of an alternative exemplary embodiment of a fluid director.
Figure 10:
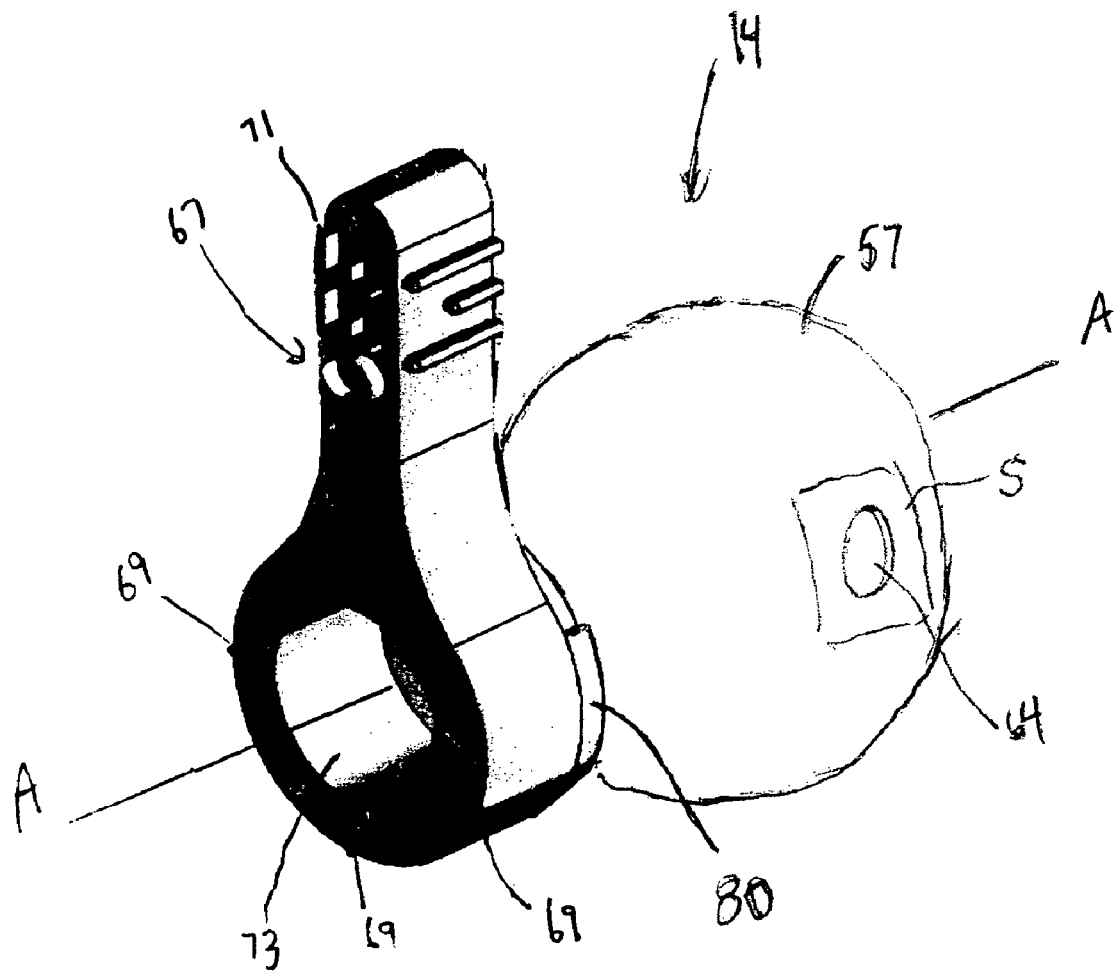
FIG. 10 is a perspective view of an alternative exemplary embodiment of a fluid director.

As shown in FIGS. 6 and 7, the connecting portion 12 may be a hollow cylindrical barrel. A fluid director 14 such as illustrated in FIGS. 6, 8 and 9 may have a cylindrical portion 53 which may be inserted into the opening 55 (FIG. 7) in connecting portion 12 such that the fluid director 14 may be positioned within the connecting portion 12 as shown in FIGS. 1A and 6. In another embodiment such as shown in FIG. 10, the fluid director 14 may have a spherical portion 57, which may be inserted into a spherical connecting portion 12 (not shown). However, it should be understood that the fluid director 14 may have portions, which may be any other shape so long as the fluid director 14 may move within the connection portion 12.

The fluid director 14 may be positioned within the connecting portion 12 so that the fluid director 14 may moved within the connection portion 12. Thus, an operator may use the fluid director 14 to direct the flow of fluid between the first port 6, 6a the second port 8 and/or the third port 10. In an embodiment with more than three ports, the fluid director 14 may be used to direct fluid flow between any and all ports.

The fluid director 14 may be made of, for example, plastic (e.g., polyethylene, low density polyethylene, linear low density polyethylene, polyester, polyurethane, polycarbonate, acrylonitrile butadiene styrene (ABS)), a composite material (i.e., two or more materials) (e.g., copolyester), or rubber. Various factors may be considered when determining the material to be used for the fluid director 14, including compatibility with fluids flowing through the fluid control device 2, 2a (i.e., material does not chemically and/or physically react with fluids flowing through the fluid control device 2, 2a) (e.g., lipid resistance), the ability to withstand sterilization/cleaning (i.e., cleaning products used in sterilization), durability, mechanical strength, resistance to bacterial formation, ease and cost of manufacturing, compressibility and resiliency.

Moreover, the fluid director 14 may be made, for example, by injection molding, extrusion, casting, compression molding or transfer molding. In addition, the fluid director 14 may be made of a single piece of material or multiple pieces attached together, for example, by a bonding medium (e.g., adhesive), threads, ultrasonic welding, ultraviolet curing, tape, corresponding clip and clip engaging portion(s) (e.g., a snap connection), spin welding or otherwise melting together. In one embodiment where the fluid director 14 may be made of two pieces, one piece may have at least one protrusion (not shown) and the other piece may have at least one recess (not shown) for receiving the at least one protrusion.

Figure 11A:
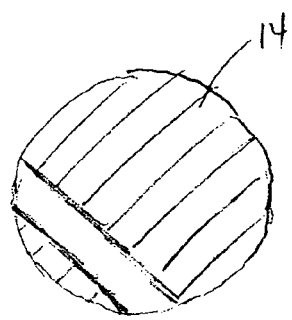
FIG. 11A-11F are cross-sectional views through the fluid director of exemplary embodiments of passageways.
Figure 11B:
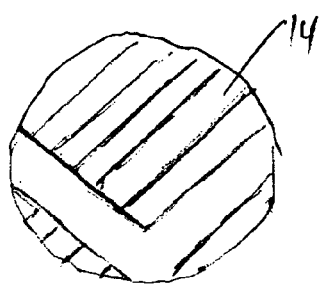
Figure 11C:
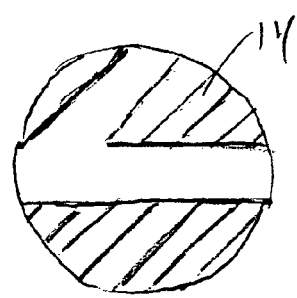
Figure 11D:
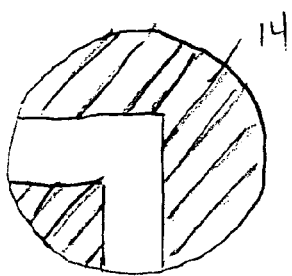
Figure 11E:
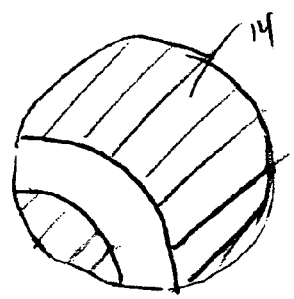
Figure 11F:
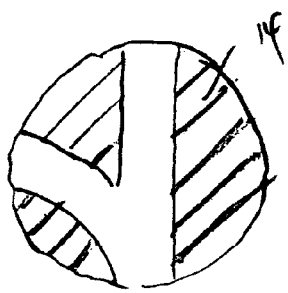
Figure 12A:
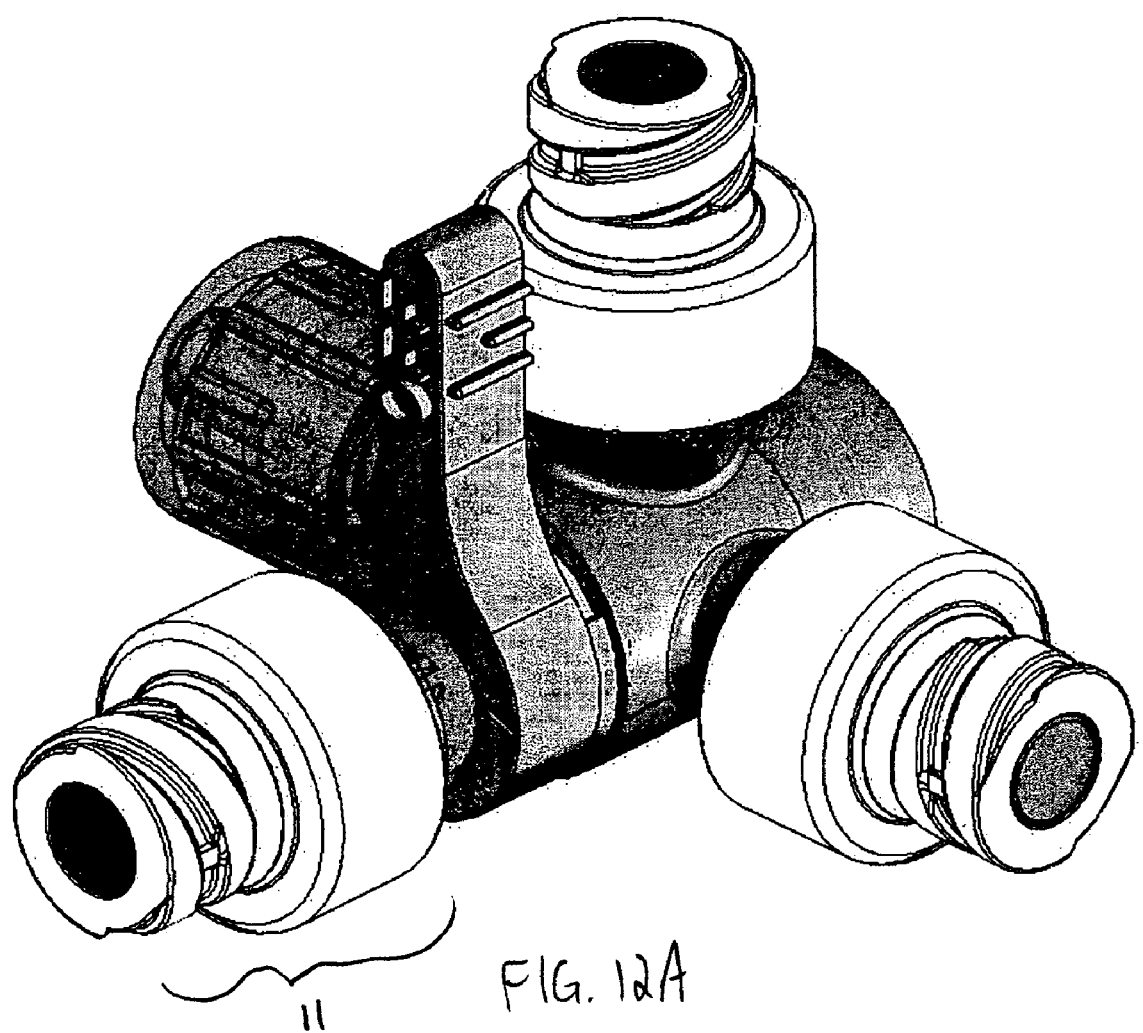
FIG. 12A is an alternative exemplary embodiment of the device of FIGS. 3A and 3B.
Figure 12B:
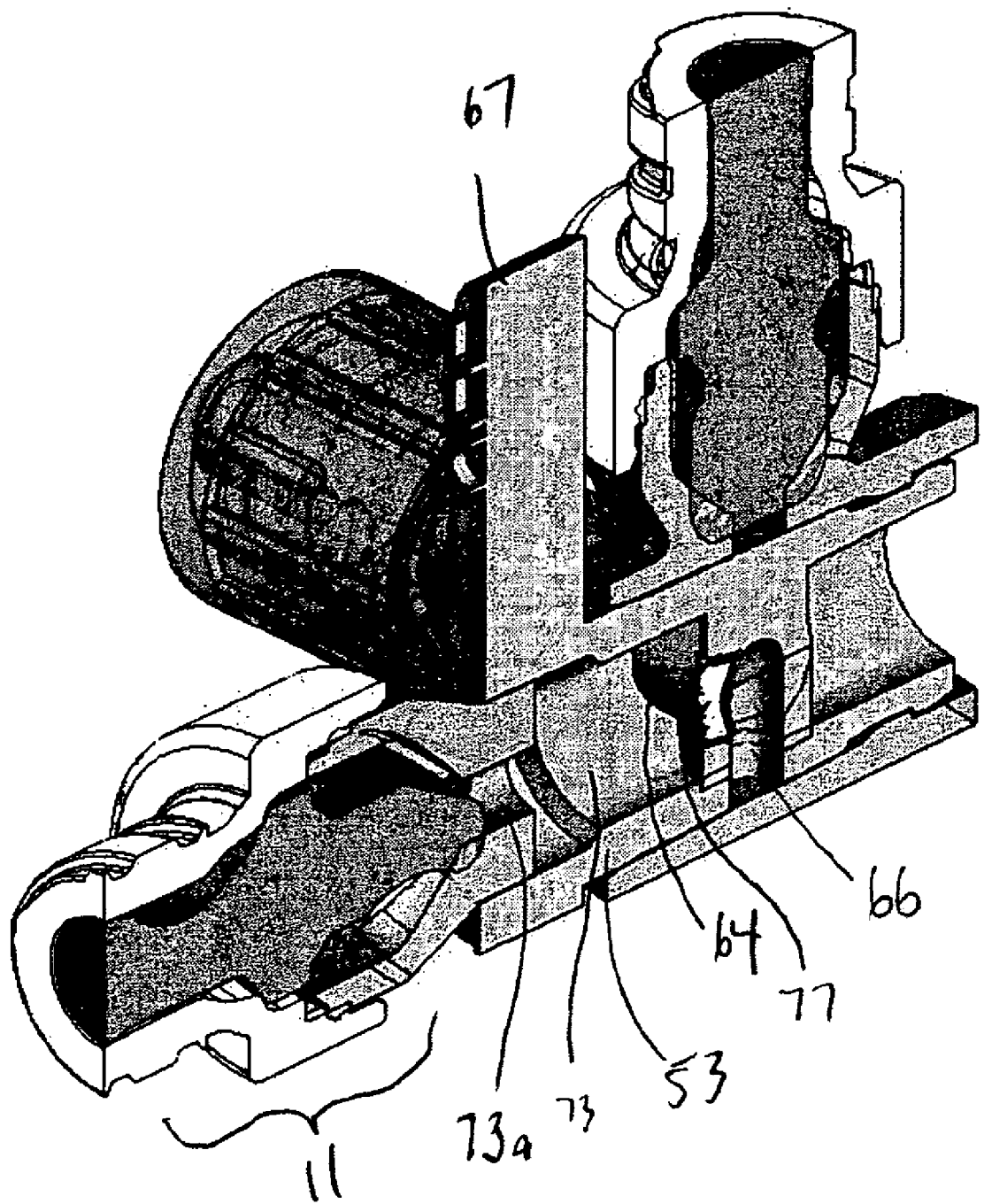
FIG. 12B is a cross-sectional view of the device of FIG. 12A.
Figure 12D:
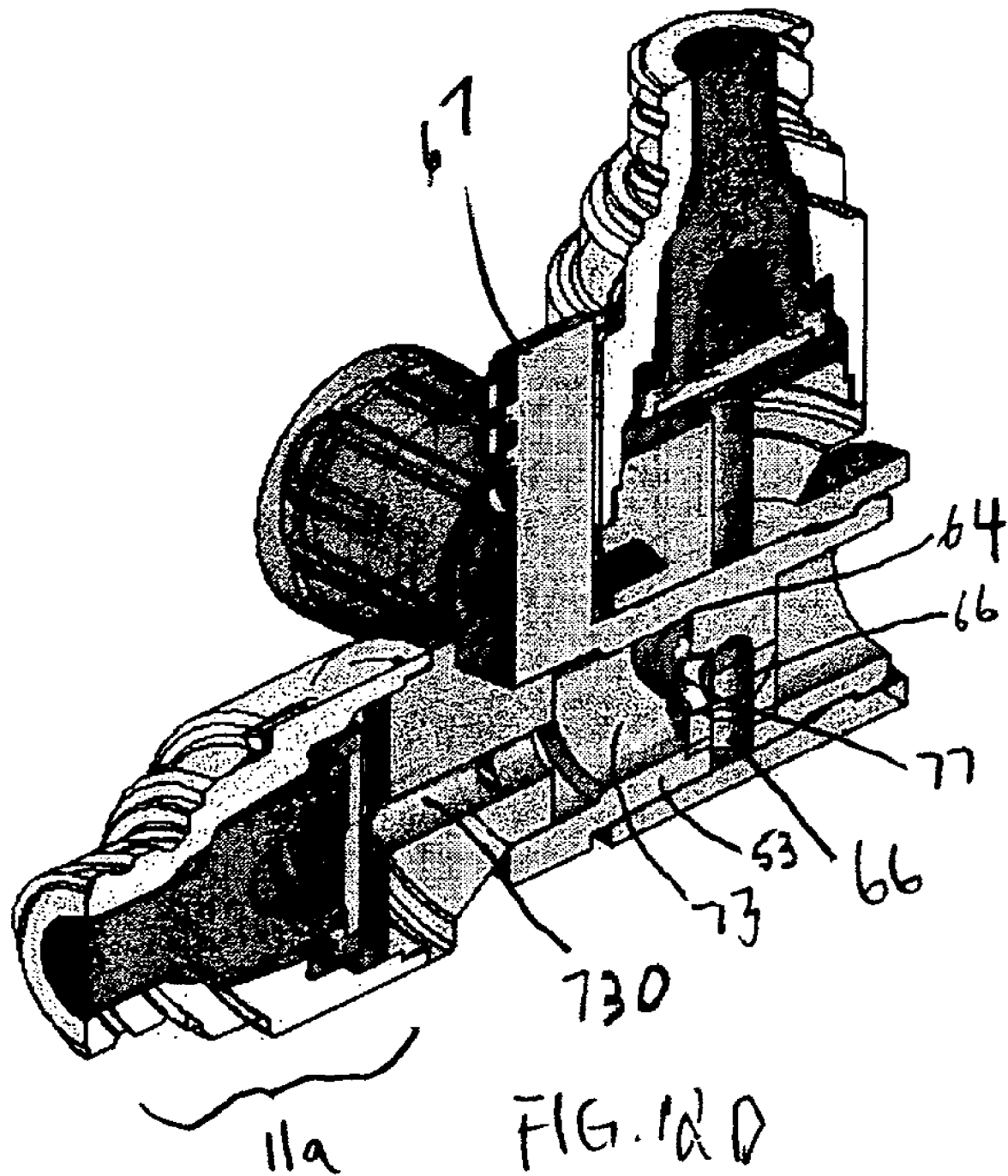
FIG. 12D is a cross-sectional view of the device of FIG. 12C.

The fluid director 14 may have one or more fluid passageways 64, 66 for placing two or more ports in fluid communication with each other. In one embodiment, the fluid passageways 64, 66 may have a diameter of between about 0.02 inches and about 0.12 inches, more preferably, between about 0.05 inches and about 0.1 inches and, most preferably, between about 0.07 inches and about 0.1 inches. As shown in FIG. 1B, the passageways 64, 66 may connect the first port 6, 6a, the second port 8 and/or the third port 10. The fluid passageways 64, 66 may be any shape and/or size. The passageways 64, 66 may be round, oval, square, rectangular, or otherwise polygonal. Further, FIGS. 11A-11F illustrate numerous arrangements of various fluid passageways through the fluid director 14. It should be noted that the fluid passageways may be straight (FIGS. 11A-11D), curved (FIG. 11E), or any other shape or combination of shapes (FIG. 11F). Moreover, where multiple fluid passageways may be used, the fluid passageways may be at any angle relative to each other. For example, as shown in FIG. 1B, the fluid passageways 64, 66 may be at a 90 degree angle relative to each other. It will be appreciated by those skilled in the art that the angles between fluid passageways 64, 66 may correspond to the angles 58, 60 and 62 between the ports 6, 6a, 8 and 10.

In order to prevent fluid from escaping and/or leaking out of the fluid control device 2, 2a as fluid flows, for example, between passageways 64, 66 and the first port 6, 6a, second port 8 and/or third port 10, the fluid director 14 may be sized to have a tight fit within the connecting portion 12. In addition, in one embodiment, the fluid director 14 may be made of a soft plastic such as polyethylene, low density polyethylene, linear low density polyethylene, polyester, or polyurethane. Such materials may enable the fluid director 14 to be deformed and/or compressed so that the fluid director 14 may be press fitted into the connecting portion 12 to create a seal between the fluid director 14 and the connecting portion 12 while, at the same time, allowing the fluid director 14 to move within the connecting portion 12.

Moreover, the construction of the fluid director 14 may enable the fluid director 14 to be inserted and/or turned in connecting portion 12. For example, as shown in FIG. 6, the fluid director 14 may be hollow and may have a wall 70 with a thickness, which may enable the fluid director 14 to deform so that the fluid director 14 may be inserted in the connecting portion 12 and fit snuggly therein. In one embodiment, the wall 70 of the fluid director may have a thickness of between about 0.005 inches and about 0.060 inches, more preferably, between about 0.010 inches and about 0.050 inches and, most preferably, between about 0.020 inches and about 0.040 inches. It should be noted that making the fluid director 14 from a soft material and/or constructing the fluid director 14 so that it may be hollow and, thus, deformable/compressible may enable and/or make it easier to move the fluid director 14 within the connecting portion 12.

In addition, a lubricant, for example, silicon oil or some other lubricant that is biocompatible (e.g., any substance that may act as a lubricant and will not harm a patient) may be used to enhance the ability of the fluid director 14 to move within the connecting portion 12 and/or assist in insertion of the fluid director 14 into the connection portion 12. The lubricant may be positioned between the fluid director 14 and the connecting portion 12.

In another embodiment, in order to prevent fluid from leaking out of the fluid control device 2, 2a, an O-ring (not shown) may be positioned around the proximal end 53a and/or the distal end 53b of the cylindrical portion 53 (FIG. 8) so that the O-ring may be positioned between the fluid director 14 and the connecting portion 12. In one embodiment, an O-ring may be positioned in the recess 65 at the distal end 53b of the cylindrical portion 53 and another O-ring may be positioned in a recess (not shown) in the proximal end 53*a* of the cylindrical portion 53.

In yet another embodiment, at least one sleeve S may be positioned around the fluid director 14 to prevent fluid for leaking out of the fluid control device 2, 2*a*. It should be noted that the sleeve S may be optional and may not be necessary in all embodiment. The sleeve S may be integral or separate from the fluid director 14 and may be made of, for example, plastic (e.g., polycarbonate, acrylonitrile butadiene styrene (ABS), polyethylene, low density polyethylene, linear low density polyethylene, polyester, polyurethane), a composite material (i.e., two or more materials) (e.g., copolyester), or rubber. Moreover, the sleeve may be transparent or opaque. Various factors may be considered when determining the material to be used for the sleeve S, including compatibility with fluids flowing through the fluid control device 2, 2*a* (i.e., material does not chemically and/or physically react with fluids flowing through the fluid control device 2, 2*a*) (e.g., lipid resistance), the ability to withstand sterilization/cleaning (i.e., cleaning products used in sterilization), durability, mechanical strength, resistance to bacterial formation, ease and cost of manufacturing, compressibility and resiliency.

The sleeve S may be a piece of material, which may be wrapped around the fluid director 14. Alternatively, the sleeve S may be sprayed on the fluid director 14. Further, sleeve S may be compressible so that it may be held firmly between portion 53 of the fluid director 14 and the connecting portion 12. The sleeve S may be any shape or size so long as its keeps the fluid within the passageways 64, 66 and first port 6, 6*a*, second port 8 and third port 10 as well as allows the fluid director 14 to move within the connecting portion 12. Moreover, the sleeve S may have a width which may be larger than the diameter or width of the passageways 64, 66.

While FIG. 8 shows a sleeve S around the entire perimeter of the portion 53, the sleeve S may be multiple pieces positioned at various locations on portion 53. For instance, as shown in FIG. 10, sleeve S may be a piece or strip of material around the openings of the passageways 64, 66. The piece(s) or strip(s) of material may be any shape (e.g. square, circular, etc.). It will be appreciated that any other construction, component or method known by those skilled in the art may be used in place of or in addition to the sleeve S, so long as it may keep fluid from escaping/leaking out of the fluid control device 2, 2*a* and may allow the fluid director 14 to move within the connecting portion 12. In another embodiment, the portion 53 may have an increased diameter portion (not shown) around the passageways 64, 66. The increased diameter portion of the fluid director 14 may tightly engage the connecting portion 12 to create a seal and/or prevent fluid from leaking out of the fluid control device 2, 2*a*.

Furthermore, as shown in FIG. 6, to eliminate and/or reduce axial movement of the fluid director 14 within the connecting portion 12, the fluid director 14 may have at least one recess 65 (FIGS. 8 and 9), which may engage at least one corresponding protrusion 65*a* around a portion of the inner periphery of the connection portion 12. The recess 65 may be an annular recess engaging an annular protrusion 65*a* of the connecting portion 12. This may enable the fluid director 14 to move rotationally but may limit or prevent axial movement of the fluid director 14 within the connecting portion 12. Alternatively, the shape of the fluid director 14 may limit the movement of the fluid director 14 within the connection portion 12 (e.g., where the fluid director 14 and connecting portion 12 may be spherical in shape (FIG. 10)). In other embodiments, the fluid director 14 may have a protrusion and the connecting portion 12 may have a recess. Such constructions may be desirable for various reasons, including keeping the fluid director 14 within the connecting portion 12 and maintaining alignment of the passageways 64, 66 of the fluid director 14 with the first port 6, 6*a* second port 8 and/or third port 10 as the fluid director 14 is moved within the connection porting 12.

Furthermore, in one embodiment, the connecting portion 12 may be closed at its ends so that the fluid director 14 may be contained therein. In such an embodiment, the connecting portion 12 may have an opening (not shown) large enough to receive a tool or other actuation mechanism for moving the fluid director 14 within the connecting portion 12. A fluid director 14, such as shown in FIG. 9, may be used in such an embodiment. Such a construction, alone or in combination with other fluid leak prevention features discussed above (e.g., sleeve S, size of fluid director 14, material used, wall thickness, O-ring), may also prevent fluid from leaking out of the fluid control device 2, 2*a*.

As shown in FIGS. 8 and 10 the fluid director 14 may comprise an actuation mechanism, such as knob 67 which may be any shape or size. The knob 67 and portions 53, 57 may be a single piece or may be separate pieces connected by a bonding medium (e.g., adhesive), threads, ultrasonic welding, ultraviolet curing, tape, corresponding clip and clip engaging portion(s) (e.g., a snap connection), spin welding or otherwise melting together. The knob 67 may be made of the same or different material as the portions 53, 57. Moreover, the knob 67 may be permanently fixed and/or removeable/attachable to the portions 53, 57.

As shown in FIGS. 1A and 8, the knob 67 may provide an operator with a visual indicator of which ports may be connected to each other by fluid passageways 64, 66 and/or which port(s) may be shut off (i.e., no fluid may flow to/from those ports). For example, the knob 67 may have arrows 69, which may show the orientation of the fluid passageways 64, 66. Additionally, the knob 67 may have a written indication 71, such as "OFF," to show which port may be shut off. There may be one or more arrows 69 and/or one or more written indications 71. In one embodiment, a written indication, such as "ON" may replace or may be used in addition to the arrows 69. In another embodiment, there may be no arrows 69 and only written indication 71 or there may be no written indication 71 and only arrows 69. It should be noted that the position of the arrows 69 and/or written indication 71 may correspond to the location and orientation of the passageways, such as passageways 64, 66, through the fluid director 14.

In another embodiment, the actuation mechanism may be a separate tool (not shown) such as a screwdriver, allen wrench, attachable knob, etc. As shown in FIG. 9, a fluid director 14 may have one or more bores 59 for receiving a tool. The bore(s) 59 may be any shape or size, depending on the tool to be used. The tool, in turn, may be used to move the fluid director 14 and, consequently, the passageways 64, 66 within the connecting portion 12.

It should be noted that an actuation mechanism, such as knob 67 and/or a tool may be used to rotate the fluid director 14 360 degrees about axis A-A (FIGS. 8 and 10) within the connecting portion 12. However, in other embodiments, the rotational movement of the fluid director 14 may be limited. As shown in FIG. 7, the connecting portion 12 may have a rotation limiting portion 79, which may engage a protrusion 80, 81 (FIGS. 1A, 2A, 8, 9 and 10) of the fluid director 14. In such a construction, the fluid director 14 may be rotated between a first position, where the protrusion 80, 81 engages side 79*a* of the rotation limiting portion 79, and a second position, where the protrusion 80, 81 engages side 79*b*. Thus, in one embodiment, the fluid director 14 may be rotated an angle about axis A-A between about 0 degrees and about 360 degrees, more preferably, between about 150 degrees and about 210 degrees and, most preferably, between about 170 degrees and about 190 degrees. In another embodiment, the fluid director 14 may be rotated an angle about axis A-A between about 0 degrees and about 180 degrees, more preferably, between about 60 degrees and about 120 degrees and, most preferably, between about 80 degrees and about 100 degrees.

In some embodiments, the limiting portion 79 and/or protrusion 80, 81 may be overridden such that the fluid director 14 may be rotated 360 degrees. For example, in an embodiment where the protrusion 80, 81 may be made of a softer material than the limiting portion 79, rotating the fluid director 14 so that the protrusion 80, 81 may push up against the limiting portion 79 may cause the protrusion 80, 81 to deform. As the force applied to the protrusion 80, 81 by the limiting portion 79 increases with rotation of the fluid director 14, the limiting portion 79 may move over, under, and/or around, and/or deform the protrusion 80, 81. In another embodiment, the limiting portion 79 may be deformed by the protrusion 80, 81 and/or the protrusion 80, 81 may move over, under and/or around under the limiting portion 79. It should be appreciated that in one embodiment, not shown, the connecting portion 12 may have more than one limiting portion 79 and/or the fluid director 14 may have more than one protrusion 80, 81. In one embodiment, some limiting portions 79 and/or protrusions 80, 81 may be overridden, while other limiting portions 79 and/or protrusions 80, 81 may not be overridden.

Furthermore, as shown in FIGS. 12A through 12D, a port 11, 11*a* may pass through the center portion 73 of the knob 67 such that fluid may flow therethrough. The port 11, 11*a* may be connected to the passageways (e.g., passageways 64, 66) within fluid director 14. In one embodiment, the bore 59 may also serve as a port, which may be connected to fluid passageways 64, 66. In such embodiments, fluid may flow through the port 11, 11*a*, through channel 73*a*, 730, into central portion 73 and through passageway 77. The passageway 77 may be connected to passageways 64, 66. In another embodiment, the port 11, 11*a* and/or channel 73*a*, 730 may be directly connected to passageway 77 such that fluid may flow directly between channel 73*a*, 730 and passageway 77. Other combinations and shapes of passageways are also envisioned. In this way, fluid flow may be directed between the port 11, 11*a* (through the fluid director 14, knob 67 and/or bore 59) and the first port 6, 6*a*, second port 8 and/or third port 10. It should be noted that the port 11, 11*a* may be integral with the fluid director 14 or a separate piece attachable to the fluid director 14. The port 11, 11*a* may be rotatable with respect to the knob 67 such that the port 11, 11*a* may be attached to a fluid transfer device without rotating the entire device 2, 2*a*.

Turning now to the second and third ports 8, 10, the second port 8 and third port 10 may have different structures as described below or the same structures as each other or the first port 6, 6*a*. It should be appreciate by those skilled in art that, in one embodiment, any opening in the connecting portion 12 may be a port so long as a fluid transfer device may be operably associated with the opening.

As shown in FIGS. 1B and 2B, the second port 8 may simply be a cylinder having a channel 68 therethrough. A fluid transfer device, such as second fluid transfer device 102, may be attached to the inside and/or outside of the second port 8. For example, an intravenous tube may be positioned within the channel 68. The second fluid transfer device 102 may be permanently or temporarily connected to the second port 8 by, for example, bonding medium (e.g., adhesive), friction (e.g., a portion of device 102 may be tapered and/or dimensioned to fit snuggly within channel 68), threads, ultrasonic welding, ultraviolet curing, tape, corresponding clip and clip engaging portion(s) (e.g., a snap connection), spin welding or otherwise melting together. In one embodiment, the second port 8 may have threads 83 (FIGS. 1A and 2A) for engaging corresponding threads of a fluid transfer device. In another embodiment, a fluid transfer device, such as an intravenous tube, may be stretched so that the fluid transfer device may fit around the second port 8. Once the intravenous tube is around the second port 8, the intravenous tube may contract towards it original size, thereby compressing onto the second port 8. A shrinkable sleeve (not shown) may be placed around the intravenous tube and the second port 8 and heated to shrink the sleeve, thereby connecting the intravenous tube and the second port 8.

Figure 13:
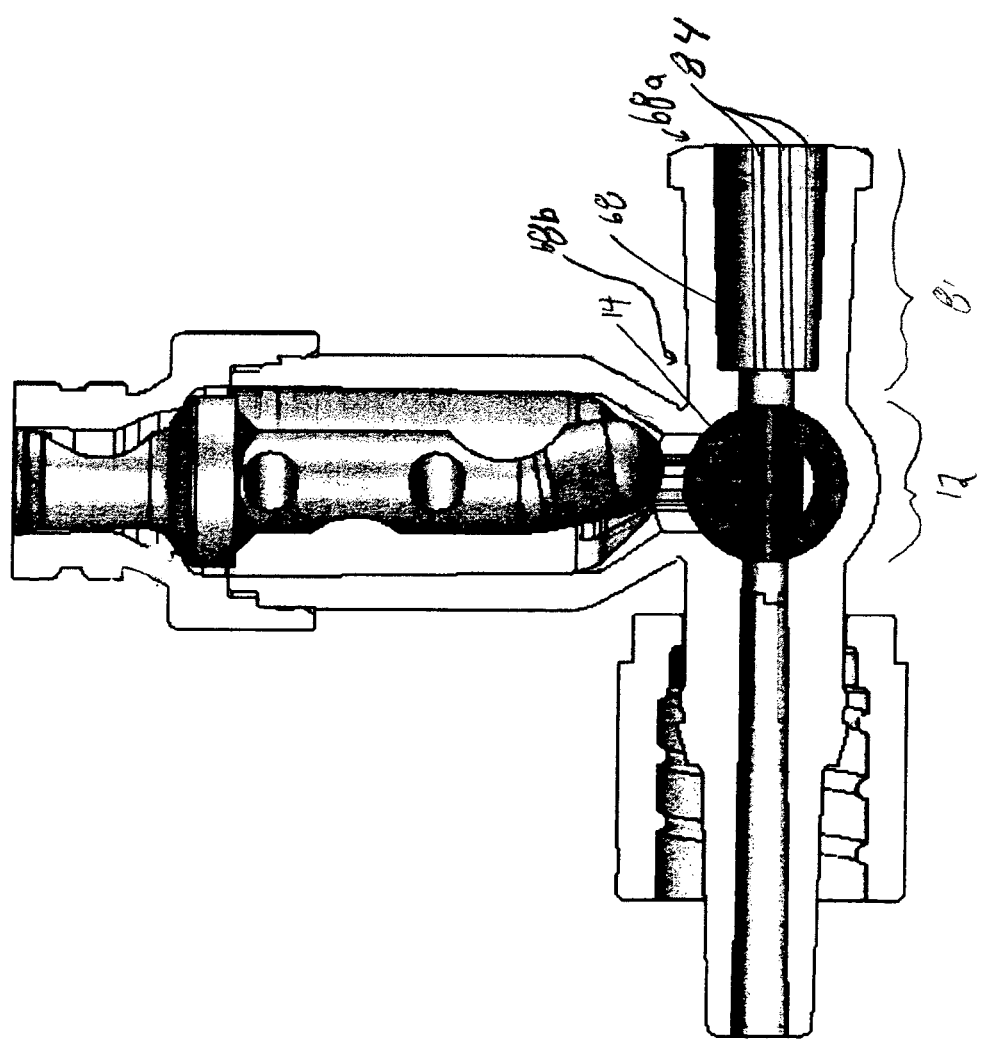
FIG. 13 is a partial cross-sectional view of the device of FIGS. 1A and 1B with an alternative second port construction.

Furthermore, as shown in FIG. 13, the second port 8 may also have one or more bonding medium reservoirs 84 which may take the form of one or more recesses or grooves in the channel 68 and which may extend a length between a proximal end 68*a* and a distal end 68*b* of the second port 8. The bonding medium reservoirs 84 may have a length, for example, between about 0.325 inches and about 0.475 inches, more preferably, between about 0.350 inches and about 0.400 inches and, most preferably, between about 0.360 inches and about 0.390 inches. In those embodiment where a fluid transfer device is connected to the outside of the second port 8, the bonding medium reservoirs 84 may also be located on the outside of the second port 8. It should be noted that in some embodiments, bonding medium reservoirs 84 may also be positioned on any surface of the third port 10.

The bonding medium reservoirs 84 may receive excess bonding medium (e.g., adhesive) when a fluid transfer device may be positioned in the channel 68 or on the outside of the second port 8 using a bonding medium. It should be understood that a bonding medium reservoir may receive any liquid material which may harden, including any solid material (e.g., solid plastic) that has been melted (e.g., as may result if a fluid transfer device is ultrasonically welded to the second port 8). Another function of the bonding medium reservoirs 84 may also be to prevent bonding medium and/or melted material from spreading into the connecting portion 12, the fluid director 14 and/or passageways 64, 66. Such a construction may be advantageous because bonding medium and/or melted material may affect the movement of the fluid director 14 and/or the overall flow of fluid through the passageways 64, 66.

Additionally, the third port 10 may have a central portion 72 with a channel 74 therethrough. The central portion 72 may be surrounded by a wall portion 76 which may contain internal threads 78 for engaging corresponding threads (not shown) of a third fluid transfer device 103. The wall portion 76 may be fixed to or rotatable about the central portion 72. In an embodiment where the wall portion 76 may be rotated about the central portion 72, the central portion 72 may comprise an engagement surface 75, which may take the form of protrusions on the central portion 72. Such a construction may allow the wall portion 76 to rotate on the central portion 72 and, at the same time, may prevent the wall portion 76 from being disengaged from the central portion 72. Providing a rotatable piece as part of the third port 10 may also enable an operator to thread the third port 10 onto the third fluid transfer device 103 without the need to rotate the entire device 2, 2*a*. Such a construction may also reduce or eliminate torque on a fluid transfer device 100, 102, 103 attached to the device 2, 2*a* and, thereby, may prevent kinking and/or movement of the fluid transfer device 100, 102, 103 as the fluid control device 2, 2*a* is being attached to a fluid transfer device 100, 102, 103.

In one embodiment, where one port 6, 6a, 8, 10 may be connected to an intravenous tube which, in turn, may be connected to a catheter inserted in a patient, such a construction may prevent spinning of the catheter in the skin of a patient. It should be noted that, in some embodiments, the second port 8 may have the same construction as the third port 10. Alternatively, the third port 10 may have the same construction as the second port 8.

As will be appreciated by those skilled in the art, any of the components of the present invention, including the specific embodiments described herein, may incorporate an antimicrobial compound or may have an antimicrobial coating covering a portion or the entire surface of the components. The antimicrobial compound or coating may inhibit the growth of bacteria. An antimicrobial material may be formed, for example, by adding a commercially available antimicrobial compound such as Agion™ produced by Agion™ Technologies Inc. of Wakefield, Mass., to, for example, plastic or rubber. The antimicrobial containing material, in turn, may be used to make a component of the present invention. Alternatively or in addition, an antimicrobial compound may be sprayed, painted or otherwise affixed to the surface of any component of the present invention and, thus, form a coating thereon.

In use, one end of the first fluid transfer device 100 (e.g., intravenous tube, syringe, catheter, or other connector) may be connected (either permanently or removeably) to the first port 6, 6a. A second fluid transfer device 102 may be connected to the second port 8 and a third fluid transfer device 103 may be connected to a third port 10. An operator may use the first port 6, 6a to transfer fluid into the fluid control device 2, 2a and/or transfer fluid from the fluid control device 2, 2a. To accomplish this, a portion (e.g, a male luer) of the first fluid transfer device 100 may be inserted into the first port 6, 6a. In the embodiments of FIGS. 1B and 2B, insertion of the first fluid transfer device 100 into the first port 6, 6a may result in compression, canting, bending, folding, and/or contorting of the first valve element 16, 160 within the first port 6, 6a (i.e., the head portion 32, 320 and/or body portion 34, 340 may compress, cant, bend, fold, and/or contort).

The first port 6, 6a may have a longitudinal axis and the first valve element 16, 160 may also have an axis, which may extend from a proximal end 29a, 290a to a distal end 29b, 290b of the first valve element 16, 160. The first valve element 16, 160 may have a first position (shown in FIGS. 1B and 2B), where the top 44, 440 of the first valve element 16, 160 may be substantially flush with the top 46, 460 of the cap 18, 180. In the first position, the axis of the first valve element 16, 160 may be aligned with, parallel to and/or co-axial with the longitudinal axis of the first port 6, 6a (i.e., the first valve element 16, 160 may be in a closed position). Further, the first valve element 16, 160 may move to a second position, where the top 44, 440 may be displaced from the top 46, 460 into the first port 6, 6a. In the second position, the axis of the first valve element 16, 160 may be displaced from and/or non-parallel to the longitudinal axis of the first port 6, 6a such that the proximal end 29a, 290a of the first valve element 16, 160 may move towards the distal end 29b, 290b of the first valve element 16, 160 (i.e., the proximal end 29a, 290a of the first valve element 16, 160 may be closer to the distal end 29b, 290b of the first valve element 16, 160). In the second position, the first valve element 16, 160 may be in an opened position. It should be understood that a second position may be any position which is not the first position.

In an exemplary embodiment where the first fluid transfer device 100 has threads (not shown) to engage the external threaded portion 22, 220 of the first port 6, 6a, as the first fluid transfer device 100 is threaded onto the first port 6, 6a the first valve element 16, 160 may compress, cant, bend, fold, and/or contort (and possibly twist) and may move further down into the first port 6, 6a. And, as the first fluid transfer device 100 moves farther into the first port 6, 6a, the first valve element 16, 160 may move out of proximal channel 26, 260 and into the main channel 30, 300. In this position, fluid may flow past the first valve element 16, 160. In FIG. 2B, insertion of the fluid transfer device 100 into the first port 6, 6a may also result in the air contained in chamber 342 to move through venting channels 343 and out of fluid control device 2a.

In an embodiment with a first enlarged portion 38, when the first valve element 16, 160 is in a closed position, fluid flow between the fluid transfer device 100 and channel 24, 240 may be prevented. When the first valve element 16, 160 is in the opened position, fluid may flow between the fluid transfer device 100 and channel 24, 240. Moreover, the flow of fluid between the proximal channel 26, 260 and the main channel 30, 300 may be prevented when the second enlarged portion 41, 410 engages an inner portion of the first port 6, 6a (e.g., shoulder portion 43, 430). Upon disengagement of the second enlarged portion 41, 410 from an inner portion of the first port 6, 6a (e.g., shoulder portion 43, 430), fluid may flow between the proximal channel 26, 260 and the main channel 30, 300.

When the first valve element 16, 160 is in a second position, fluid may be transferred to the first port 6, 6a from the first fluid transfer device 100 and flow through the fluid control device 2, 2a. Where fluid may already be present in the fluid control device 2, 2a, the fluid from the device 100 may combine with the fluid already within the device 2, 2a. It should be understood that the term "combine" can mean that the first and the second fluid join to form a homogenous third fluid (e.g., dilution of a medication in saline) or that the first and second fluids may remain separate from one another (e.g., blood in water; oil in water). Alternatively, the first fluid may be transferred to the first fluid transfer device 100 from the first port 6, 6a (i.e, fluid may be withdrawn from the fluid control device 2, 2a).

In general, with reference to FIGS. 1B and 2B, when fluid is transferred from the first fluid transfer device 100 to the first port 6, 6a, the fluid may flow past the valve element 16, 160 into and through the passageways 64, 66 of the fluid director 14 and into the second and/or third ports 8, 10. Fluid may then flow into the second and/or third fluid transfer devices 102, 103. In one embodiment of FIG. 1B, fluid may pass through the channels 56 as the fluid flows between the first port 6 and the connecting portion 12.

Alternatively, fluid may flow in the opposite direction when fluid is transferred from the second and/or third ports 8, 10 to the first fluid transfer device 100. Moreover, in the embodiment of FIG. 2B, fluid may flow past the first valve element 160 and flow in between ribs 161, around the circular flange 162, into and through fluid port 163 and out channel 164. Alternatively, fluid may flow in the opposite direction when fluid is transferred from the second port 8 and/or third port 10 to the transfer device 100.

If and when the first fluid transfer device 100 is removed from the first port 6, 6a, the first valve element 16, 160 may return to its first position (e.g., with the top 44, 440 of the first valve element 16, 160 substantially flush with the top 46, 460). In such a position fluid may be prevented from flowing past the first valve element 16, 160.

In the embodiment of FIG. 2B, as the valve element 160 moves from the second (opened) position to the first (closed) position (e.g., when the fluid transfer device 100 is removed from the first port 6a), air may flow from outside the fluid control device 2a through venting channels 343 and into chamber 342. Such a construction may result in positive pressure or self-flushing (e.g., fluid may flow in a direction 350 out of the fluid control device 2, 2a, second port 8 and/or third port 10 and/or towards a patient). It should be understood that any self-flushing construction may be integrated into the fluid control device 2, 2a, such as those constructions disclosed in U.S. Pat. No. 5,730,418, which is incorporated herein by reference. In FIG. 1B, negative pressure (e.g., where fluid may flow into the fluid control device 2, 2a, second port 8 and/or third port 10 and/or away from a patient) may result if and when the fluid transfer device 100 is removed from the first port 6. In the embodiment of FIG. 2B, negative pressure may result when the fluid transfer device 100 is inserted into the first port 6a.

It should be noted that the operation of the valve element 16, 160 may be the same regardless of whether the valve element 16, 160 may be a second valve element positioned in the second port 8 (FIGS. 3A, 3B, 4A, and 4B), a third valve element positioned in the third port 10 and/or a fourth valve element positioned in the port 11, 11a (FIGS. 12A through 12D).

Moreover, an operator may use the actuation mechanism, for example, knob 67 or other tools (e.g., screwdriver, allen wrench), to orient the fluid director 14 such that fluid may be directed between various ports. At least one passageway of the fluid director 14 may be aligned so as to connect two or more of the first port 6, 6a, the second port 8 and the third port 10. In an embodiment where the fluid director 14 may comprise visual indicators such as arrows 69 and written indication 71, the arrows 69 may be aligned with the ports to be connected and the written indication 71, such as "OFF," may be aligned with the port(s) that may not be connected to other ports (i.e., the port that may be shut off).

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

What is claimed is:

1. A fluid control device for transferring fluid comprising: a monolithic housing having a first port, a second port, a third port, and a connecting portion connecting the first, second and third ports, the first port having a longitudinal axis; a needleless access device incorporated into the first port, the needleless access device including a first valve element positioned within the first port, the first valve element having a proximal end, a distal end, an axis, a first position when the needleless access device is not actuated where the axis of the first valve element is parallel with the longitudinal axis of the first port, and a second position when the needleless access device is actuated where the axis of the first valve element is displaced from the longitudinal axis of the first port; a fluid director having at least one fluid passageway, wherein the fluid director is positionable within the housing; and an actuation mechanism operably associated with the fluid director, wherein the actuation mechanism is sized and configured to move the fluid director.

2. The device of claim 1, wherein the first valve element comprises a head portion and a body portion.

3. The device of claim 2, wherein at least one of the head portion and the body portion comprises at least one notch.

4. The device of claim 2, wherein the body portion comprises a wall defining a chamber, wherein the chamber contains air.

5. The device of claim 4, wherein the first port comprises at least one venting channel in communication with the chamber, the at least one venting channel sized and configured to allow air to move between inside the chamber and outside the chamber.

6. The device of claim 2, wherein the proximal end of the first valve element comprises a first enlarged portion.

7. The device of claim 6, wherein the first valve element comprises a second enlarged portion between the first enlarged portion and the distal end of the first valve element.

8. The device of claim 1, wherein the first valve element is made of an elastomeric material.

9. The device of claim 1, wherein the first port further comprises a valve seat having at least one rib, the first valve element being operably associated with the valve seat.

10. The device of claim 1, wherein the first valve element has a length between about 0.15 inches and about 1.5 inches.

11. The device of claim 10, wherein the first valve element has a length between about 0.4 inches and about 0.6 inches.

12. The device of claim 1, wherein the fluid director comprises a first and second fluid passageway, the first fluid passageway being at an angle relative to the second fluid passageway.

13. The device of claim 12, wherein the fluid director has at least one visual indicator to indicate the orientation of the first and second fluid passage ways relative to at least one of the first, second and third ports.

14. The device of claim 1, wherein the fluid director comprises at least one bore and the actuation mechanism is a toll, the tool being sized and configured to be positionable within the at least one bore.

15. The device of claim 1, wherein the fluid director comprises an outer surface and a recess on the outer surface, and wherein the connecting portion comprises an inner surface and a protrusion on the inner surface, the protrusion being moveable along the recess thereby eliminating axial movement of the fluid director within the connecting portion.

16. The device of claim 1, wherein a portion of the fluid director has a spherical shape.

17. The device of claim 1, wherein the actuation mechanism is a knob.

18. The device of claim 17, further comprising a fourth port through the knob, wherein the fourth port is sized and configured such that fluid flows between the fourth port and the at least one fluid passageway.

19. The device of claim 1, wherein the fluid director is made of a soft material selected from the group consisting of polyethylene, low density polyethylene, linear low density polyethylene, polyester, and polyurethane.

20. The device of claim 1, wherein at least one of the housing, the first valve element, the fluid director and the actuation mechanism comprises an antimicrobial component.

21. The device of claim 1, wherein the connecting portion comprises a limiting portion with a first end and a second end and the fluid director comprises a protrusion, wherein the fluid director is sized and configured to move between a first location, where the protrusion engages the first end of the limiting portion, and a second location, where the protrusion engages the second end of the limiting portion.

22. The device of claim 1, further comprising at least one sleeve positioned on the fluid director, wherein the sleeve is located between the fluid director and the connecting portion.

23. The device of claim 1, wherein the fluid director comprises a wall having a thickness between about 0.005 inches and about 0.060 inches.

24. The device of claim 23, wherein the fluid director comprises a wall having a thickness between about 0.020 inches and about 0.040 inches.

25. The device of claim 1, wherein at least one of the second and third ports has an inner surface, an outer surface, a distal end proximate the connecting portion, a proximal end opposite the distal end, and at least one bonding medium reservoir, the at least one bonding medium reservoir is at least one recess in at least one of the inner surface and the outer surface and extends a length between the proximal end and the distal end of at least one of the second and third ports.

26. The device of claim 1, wherein at least one of the second and third ports comprises:
   a central portion having a channel therethrough; and
   a wall portion having an inner and outer surface, the inner surface having threads, wherein the wall portion is sized and configured to rotate about the central portion.

27. The device of claim 1, wherein the second port contains a second valve element.

28. The device of claim 27, wherein the third port contains a third valve element.

29. A fluid control device for transferring fluid comprising: a monolithic housing having a first port, a second port, a third port and a connecting portion connecting the first port, the second port, and the third port; an access port in the first port for allowing fluid to be injected into the fluid control device, the access port including a first valve element positioned within the first port, the first valve element having a proximal end and a distal end, wherein the first valve element has an opened position allowing fluid to be injected into the fluid control device and a closed position, and wherein the first valve element is sized and configured such that the proximal end of the first valve element is closer to the distal end of the first valve element in the opened position than in the closed position; a fluid director having at least one fluid passageway, wherein at least a portion of the fluid director is positionable within the connecting portion; and an actuation mechanism operably associated with the fluid director, wherein the actuation mechanism is sized and configured to move the fluid director.

30. The device of claim 29, wherein the first valve element comprises at least one notch.

31. The device of claim 29, wherein the first valve element comprises a head portion and a body portion.

32. The device of claim 31, wherein the body portion comprises a wall defining a chamber, the chamber containing air.

33. The device of claim 32, wherein the first port comprises at least one venting channel in communication with the chamber, the at least one venting channel sized and configured to allow air to move between inside the chamber and outside the chamber.

34. The device of claim 33, wherein the first valve element has a length between about 0.3 inches and about 1.5 inches.

35. The device of claim 34, wherein the first valve element has a length between about 0.55 inches and about 0.75 inches.

36. The device of claim 29, wherein the actuation mechanism is a knob, and wherein the fluid director is sized and configured such that movement of the knob results in movement of the fluid director.

37. The device of claim 36, further comprising a fourth port through the knob, wherein the fourth port is sized and configured so that fluid flows between the fourth port and the at least one passageway.

38. The device of claim 37, wherein the fourth port is sized and configured to rotate relative to the knob.

39. The device of claim 29, wherein the connecting portion comprises a limiting portion with a first end and a second end, and the fluid director comprises a protrusion, wherein the fluid director is sized and configured to move between a first location, where the protrusion engages the first end of the limiting portion, and a second location, where the protrusion engages the second end of the limiting portion.

40. A method of transferring fluid comprising: providing a fluid control device comprising: a monolithic housing having a first port, a second port, a third port, and a connecting portion connecting the first, second and third ports, the first port having a longitudinal axis; a needleless access device incorporated into the first port, the needleless access device including a first valve element having an axis; a fluid director having at least one fluid passageway, wherein the fluid director is positionable within the connecting portion; and an actuation mechanism operably associated with the fluid director; inserting a first fluid transfer device into the needleless access device such that the first valve element moves from a first position, where the axis of the first valve element is parallel with the longitudinal axis of the first port, to a second position, where the axis of the first valve element is displaced from the longitudinal axis of the first port thereby permitting fluid to flow from the first fluid transfer device into the fluid control device; moving the fluid director in the connecting portion using the actuation mechanism; and aligning the at least one fluid passageway with at least two of the first, second and third ports.

41. The method of claim 40, wherein the first valve element comprises a wall defining a chamber containing air, and the first port comprises at least one venting channel, the method further comprising:
   moving air out of the chamber and through the at least one venting channel as the first valve element moves from the first position to the second position.

42. The method of claim 40, wherein the connecting portion comprises a limiting portion with a first end and a second end and the fluid director comprises a protrusion, wherein the step of moving the fluid director comprises rotating the fluid director between a first location, where the protrusion engages the first end of the limiting portion, and a second location, where the protrusion engages the second end of the limiting portion.

43. The method of claim 40 further comprising:
   engaging a second fluid transfer device with the second port; and
   engaging a third fluid transfer device with the third port.

44. The method of claim 43, wherein at least one of the second and third ports comprises an elongated central portion having a channel and a wall portion positioned around the elongated central portion, the wall portion having threads, the method further comprising rotating the wall portion on the elongated central portion so that the threads of the wall portion engage a threaded portion of at least one of the second and third fluid transfer devices.

45. A method of transferring fluid comprising: providing a fluid control device comprising: a monolithic housing having a first port, a second port, a third port, and a connecting portion connecting the first, second and third ports; a needleless access device incorporated into the first port and including a first valve element having an outer surface, a proximal end, a distal end, an opened position and a closed position, the first valve element being positioned within the needleless access device; a fluid director having at least one fluid passageway, wherein at least a portion of the fluid director is positionable within the housing; and an actuation mechanism operably associated with the fluid director; inserting a first fluid transfer device into the needleless access device such that the proximal end of the first valve element moves towards the distal end of the first valve element; moving the fluid director in the housing the actuation mechanism; aligning the at least one fluid passageway with at least two of the first, second and third ports; and allowing fluid to flow around the outer surface of the first valve element.

46. The method recited in claim 45, further comprising the step of:

transferring fluid through at least one of the second and third ports in at least one of a first direction out of the fluid control device and a second direction into the fluid control device;

wherein the first valve element causes movement of fluid through at least one of the second and third ports in the second direction in response to movement of the first valve element from the closed position to the opened position, and wherein the first valve element causes movement of fluid through at least one of the second and third ports in the first direction in response to movement of the first valve element from the opened position to the closed position.

* * * * *